US009630003B2

(12) United States Patent
Thompson et al.

(10) Patent No.: US 9,630,003 B2
(45) Date of Patent: Apr. 25, 2017

(54) NON-INVASIVE NEURO STIMULATION SYSTEM

(75) Inventors: Thomas C. Thompson, Fairview, TX (US); Martyn S. Abbott, Dallas, TX (US); Gary L. Byars, Richardson, TX (US); Garnet E. Dupuis, Santa Monica, CA (US); Vladimir P. Tepin, Taganrog (RU)

(73) Assignee: HTK ENTERPRISES, INC., Richardson, TX (US)

( * ) Notice: Subject to any disclaimer, the term of this patent is extended or adjusted under 35 U.S.C. 154(b) by 0 days.

(21) Appl. No.: 11/523,781

(22) Filed: Sep. 19, 2006

(65) Prior Publication Data
US 2007/0293918 A1    Dec. 20, 2007

Related U.S. Application Data

(63) Continuation-in-part of application No. 11/454,186, filed on Jun. 15, 2006, now abandoned.

(51) Int. Cl.
*A61N 1/04* (2006.01)
*A61N 1/36* (2006.01)
(Continued)

(52) U.S. Cl.
CPC ....... *A61N 1/36021* (2013.01); *A61N 1/0476* (2013.01); *A61N 1/08* (2013.01);
(Continued)

(58) Field of Classification Search
USPC ... 607/2, 3, 8, 46, 50, 62, 72, 115–116, 145, 607/149–150
See application file for complete search history.

(56) References Cited

U.S. PATENT DOCUMENTS 3,894,532 A * 7/1975 Morey .......................... 600/547
4,112,923 A * 9/1978 Tomecek ....................... 600/11
(Continued)

FOREIGN PATENT DOCUMENTS

JP      09-327521      12/1997
JP      2003-245363    9/2003
(Continued)

OTHER PUBLICATIONS

SCENAR Basic Introduction to Scenar Therapy Training Course, 25 pages, The Scenar Training Centre Ltd.
(Continued)

*Primary Examiner* — Carl H Layno
*Assistant Examiner* — Jennifer Ghand
(74) *Attorney, Agent, or Firm* — Edwin S. Flores; Daniel J. Chalker; Chalker Flores, LLP

(57) ABSTRACT

A device (10, 50, 60, 70, 80, 90) is used to apply an electric pulse or spike to a patient to treat the patient. The device can have a series of preset treatments programmed therein. A user can select a treatment from menus displayed on a display (100). The impedance of the skin and underlying tissue to be treated can be measured prior to the treatment to locate active areas on the skin for treatment. A variety of probes can be used with the device, with the device automatically detecting the type of probe attached. Multiple electrodes can be used on the probe, which allows the active areas in contact with the probe to be identified prior to treatment to allow the treatment to concentrate on the active areas.

29 Claims, 24 Drawing Sheets

(51) Int. Cl.
   *A61N 1/08*     (2006.01)
   *A61N 1/32*     (2006.01)
   *A61N 1/372*    (2006.01)

(52) U.S. Cl.
   CPC .......... *A61N 1/328* (2013.01); *A61N 1/36003* (2013.01); *A61N 1/37247* (2013.01)

(56) References Cited

U.S. PATENT DOCUMENTS

| | | | |
|---|---|---|---|
| 4,238,726 A | 12/1980 | Ichijo | |
| 4,292,980 A | 10/1981 | Suzuki | |
| 4,541,432 A * | 9/1985 | Molina-Negro et al. | 607/46 |
| 4,736,752 A | 4/1988 | Munck et al. | |
| 5,058,582 A | 10/1991 | Thaler | |
| 5,123,413 A | 6/1992 | Hasegawa et al. | |
| 5,281,219 A | 1/1994 | Kallok | |
| 5,284,135 A | 2/1994 | Lopin | |
| 5,304,207 A | 4/1994 | Stromer | |
| 5,540,735 A | 7/1996 | Wingrove | |
| 5,562,707 A | 10/1996 | Prochazka et al. | |
| 5,584,863 A | 12/1996 | Rauch et al. | |
| 5,947,897 A | 9/1999 | Otake | |
| 6,026,327 A * | 2/2000 | Dervieux | 607/46 |
| 6,038,485 A | 3/2000 | Axelgaard | |
| 6,041,259 A | 3/2000 | Agarwala et al. | |
| 6,083,253 A | 7/2000 | Ogama | |
| 6,219,568 B1 | 4/2001 | Kelly et al. | |
| 6,296,636 B1 * | 10/2001 | Cheng et al. | 606/32 |
| 6,301,500 B1 | 10/2001 | Van Herk et al. | |
| 6,334,069 B1 | 12/2001 | George et al. | |
| 6,393,319 B1 | 5/2002 | Bock et al. | |
| 6,413,255 B1 | 7/2002 | Stern | |
| 6,427,083 B1 | 7/2002 | Owen et al. | |
| 6,522,927 B1 | 2/2003 | Bishay et al. | |
| 6,564,079 B1 | 5/2003 | Cory et al. | |
| 6,671,547 B2 * | 12/2003 | Lyster et al. | 607/6 |
| 6,701,185 B2 | 3/2004 | Burnett et al. | |
| 6,973,344 B2 | 12/2005 | Finneran et al. | |
| 7,483,734 B2 * | 1/2009 | Colthurst | 600/547 |
| 8,457,759 B2 * | 6/2013 | Parker | A61N 1/3605 607/62 |
| 2002/0010498 A1 * | 1/2002 | Rigaux et al. | 607/62 |
| 2002/0143373 A1 | 10/2002 | Courtnage et al. | |
| 2003/0023134 A1 * | 1/2003 | Tracey | 600/29 |
| 2003/0120170 A1 * | 6/2003 | Zhu et al. | 600/547 |
| 2003/0120328 A1 * | 6/2003 | Jenkins | A61N 1/0529 607/116 |
| 2003/0187491 A1 | 10/2003 | Greenberg et al. | |
| 2003/0233129 A1 * | 12/2003 | Matos | 607/5 |
| 2004/0199216 A1 | 10/2004 | Lee et al. | |
| 2005/0131493 A1 | 6/2005 | Boveja et al. | |
| 2005/0278001 A1 | 12/2005 | Qin et al. | |
| 2006/0013543 A1 | 1/2006 | Walt et al. | |
| 2006/0052834 A1 * | 3/2006 | Goroszeniuk | 607/46 |
| 2006/0111750 A1 * | 5/2006 | Bowers | 607/5 |
| 2007/0293918 A1 * | 12/2007 | Thompson et al. | 607/72 |
| 2008/0027507 A1 * | 1/2008 | Bijelic et al. | 607/48 |

FOREIGN PATENT DOCUMENTS

| | | |
|---|---|---|
| RU | 2191042 C2 | 10/2002 |
| RU | 2244574 C2 | 1/2005 |
| WO | WO 03/018118 | 3/2003 |

OTHER PUBLICATIONS

SCENAR web pages, copyright 2003, 5 pages, The Scenar Training Centre Ltd.
International Preliminary Report on Patentability, Chapter II, PCT App PCT/US07/13659, related to claims as originally filed.

* cited by examiner

SAVES DOSE VALUES ON THE RIGHT OF THE SCREEN
SAVES HIGHEST DOSE AND THEN TWO LOWER

INDICATES COMPLETION WITH A CHECK
MARK WHEN DOSE VALUES PEAK AND THEN
2 LOWER OR WHEN 8 DOSES COMPLETED

INDICATED TO SLIDE THE DEVICE IN 4
DIRECTIONS AFTER PROCEDURE IS COMPLETE

LOW PASS FILTER FREQUENCY RESPONSE

NON-INVASIVE NEURO STIMULATION SYSTEM

CROSS REFERENCE TO RELATED APPLICATIONS

This application is a continuation-in-part of U.S. patent application Ser. No. 11/454,186 filed Jun. 15, 2006 now abandoned.

TECHNICAL FIELD OF THE INVENTION

This invention related to treatment of a human or animal using a non-invasive neuro stimulation system.

BACKGROUND OF THE INVENTION

The human body suffers many ailments. A neuro-stimulation device has been developed that has been found effective for treating many ailments, and in particular the pain associated with these ailments. Among the ailments treated are acute injuries, speeding recovery from major orthopedic surgery of joints and osteoarthritis, and the associated edema of these ailments, just to name a few. Early versions of the technology were developed in Russia and included an electronic circuit to provide a relatively high voltage, but short duration, electric pulse train to the skin of the patient. The voltage can be high, for example, with a very fast rise and fall time oscillatory pulse but with only a benign amount of energy transferred to the patient. Many of the parameters of the device can be varied to deliver the pulse train in many ways. Devices of this type can be referred to as electro stim devices and typically include a pulse generator and a control mechanism to control the pulse generator whereby the skin of the patient forms part of an LCR circuit absorbing the energy of the pulse. This type of device enables determination of the skin impedance. One example of this type of electro stim device is the SCENAR (Self Controlled Energo Neuro Adaptive Regulator) device found in Russia.

SUMMARY OF THE INVENTION

In accordance with a one aspect of the present invention, a device is provided with an electronic control mechanism to apply a relatively high voltage, but short duration, electric pulse train to the skin of the patient. The voltage can be high, with a very fast rise and fall time oscillatory pulse, but with only a benign amount of energy transferred to the patient. Many of the parameters of the device can be varied to deliver the pulse train in multiple ways. The control has at least one preset treatment parameter for setting certain pulse generator variables to generate a series of defined pulses. An interface can be provided to allow the operator of the device to select a preset treatment parameter from a menu or menus.

In accordance with another aspect of the present invention, the control has a display to show a well understood modified injury curve which shows the progression of recovery from the injury. An example would be the recovery curve after an acute athletic injury which is well known to athletic therapists and trainers. Preset treatment parameters can be developed for various stages of injury recover that correspond to the injury curve. The device would display the injury curve and provide the user access to previously determined best preset parameters that optimize recovery for that stage of the injury. The device could also display words or characters that identify stages on the curve, for example, that could then be selected to select preset parameters to treat the selected stage. In other words, the user, by understanding the stage of injury on the injury curve, can access through the display previously determined preset parameters. Further, preset treatment parameters can be developed for specific conditions, such as acute, chronic or inflamed. The device will allow the user access to previously determined best preset parameters that would treat each of these conditions, for example.

In the past, a single pulse generated by the pulse generator was used to both treat the patient and at the same time be part of a circuit that determines the relative impedance of the skin. The disadvantage of this approach is that all treatment pulses change the impedance of the skin. Repeated measurements therefore provide different results. It is important to understand that the absolute value of skin impedance is determined by many parameters, such as skin type, moisture, electrode pressure and contact area. In accordance with another aspect of the present invention, a device is provided for selectively applying an impedance sensing pulse which uses parameters lower than typically required for effective treatment so that they have minimal effect on skin impedance. The impedance sensing pulse is applied to the skin at selected locations to measure the relative impedance of the body in those locations. This allows the selection of the most efficacious location for treatment with the treatment pulse. (hereinafter referred to as the "active area" or "site") It is generally accepted that the lower impedance areas of skin provide greater treatment efficacy and are thus the active areas.

In accordance with another aspect of the present invention, the device has a monitoring circuit to generate either a visual signal or an audio signal representative of the measured relative impedance. This is particularly useful to monitor changing skin conditions as the treatment progresses by varying the audio frequency or visual signal as the measured relative impedance changes under the treatment. This allows the user to locate active sites on the skin.

The device could further include a phase detection circuit to measure the components of impedance to isolate the capacitance and resistance. This determination is made possible by effectively measuring the voltage, current and phase relationship of pulses delivered to the skin. This might give an indication that the skin is too wet or too dry for proper treatment, for example.

In accordance with another aspect of the present invention, a device is provided for applying a controlled electronic pulse to the skin of a patient. The device includes a pulse generator for generating the pulse and a control for controlling the pulse generator. Another aspect of the invention is to calculate the charge delivered to the skin of the patient by integrating the instantaneous current with time. This facilitates maintaining a constant delivered charge irregardless of variations in skin impedance as the device is moved over the skin. The ability to measure applied charge also assists in maintaining a consistent perception of stimulation for a variety of stimulation signal parameters.

In accordance with another aspect of the present invention, a device is provided for applying a controlled electronic pulse to a selected portion of the tissue of the patient through the skin of the patient. The device includes a pulse generator for generating the pulse and a control for controlling the pulse generator. The pulse is delivered to the patient by the circuit, which includes the impedance of the skin. Therefore, as the impedance of the skin changes with treatment, the treatment wave form will change.

In the past, once delivery parameters are set, changing the pulse repetition rate or number of pulses in a pulse train are not considered in new measurements of energy applied to the skin. As a result, some parameters which have variable components deliver more energy during certain portions of the delivery cycle. For example, if the pulse repetition rate of the pulses delivered doubles, the energy delivered to the patient doubles, and this energy change is perceived by the patient.

In accordance with another aspect of the present invention, a device is provided for applying a controlled electronic pulse to the skin of a patient. The device includes a pulse generator for generating the pulse and a control for controlling the pulse generator. The device further includes a circuit for normalizing the effect of the pulse on the patient, the control adjusting the conditions of the electronic pulse to maintain a uniform perceived stimulation sensation as the patient is treated. For example, for an identical wave form, a higher repetition rate equates to more energy delivered to the patient. Two pulses of higher amplitude may equate to four pulses of lower amplitude, for example. If too much energy is delivered, the pulses may be reduced in amplitude to reduce the rate of energy delivered.

In accordance with another aspect of the present invention, a device is provided for applying a controlled electronic pulse to the skin of a patient. The device includes a pulse generator for generating the pulse, a control for controlling the pulse generator and a probe. The probe is an apparatus in primary contact with the skin of the patient and has at least two electrodes for contacting the skin. The probe may be of various designs with two or more electrodes for transmitting the pulse to the skin of the patient. The device automatically identifies the type of probe that is connected to the device. The device then has the option to restrict the output of the device to appropriate modes of operation for the chosen probe or to normalize operating parameters between probes.

The probe is removable to permit the use of a second probe having a different design.

As the device is capable of automatically identifying the type of probe connected to the device, an attempt to connect an unauthorized or non-standard probe will be detected by the device and the device will not permit energy pulses to be delivered to the unauthorized or non-standard probe as a safety precaution.

In accordance with another aspect of the present invention, the device includes an automatic method for adjusting the level of stimulation. Previously, manual adjustment of the stimulation amplitude has been required. The device automatically increases the stimulation setting while simultaneously monitoring skin impedance. Changes in skin impedance as a function of the amplitude allow the optimum stimulation amplitude setting to be determined. This method is particularly useful when the device is used in the home or when the user lacks clinical training.

In accordance with another aspect of the present invention, a device is provided for applying a controlled electronic pulse to the skin of a patient. The device includes a pulse generator for generating the pulse, a control for controlling the pulse generator and a probe for transmitting the pulse to the skin of the patient. The probe has multiple electrodes for contacting the skin, which conform to the skin to provide even contact. Alternatively, multiple electronic probes can be attached to a single device which allows spaced areas on the patient to be treated simultaneously. The treatment pulses can be applied simultaneously, effectively simultaneously by multiplexing or sequentially to the probes. For example, two or three probes could be placed at different locations on a patient and pulses supplied from a single device to all the probes simultaneously, or to each probe in sequence. The device can also have multiple pulse generators, each generator supplying one or more probes.

In accordance with another aspect of the present invention, a device is provided for applying a controlled electronic pulse to the skin of a patient. The device includes a pulse generator for generating the pulse, a control for controlling the pulse generator and a probe for transmitting the pulse to the skin of the patient. The probe has an array of electrodes, adjacent electrodes being of opposite polarities. As an active area on the skin is of lower impedance, the electrode contacting that active area will experience higher current flow to the area due to the lower impedance, thus delivering more energy to the active area, as desired. The electrode array spacing needs to be sufficient to prevent touching the electrodes to each other and adequately spaced to allow effective stimulation over the entire area to be treated. The spacing between edges of adjacent electrodes is preferably at least about 0.1 inches, it can be about 0.22 inches for example, and preferably not greater than about 0.5 inches and even more preferably not greater than about 1 inch. The array of electrodes is intended to be applied in a fixed position on the body for the entire treatment, in contrast to past treatment protocols whereby the electrodes are moved by an operator from one location to another. As a result, certain combinations of treatment parameters have been developed which are timed and changed automatically to be delivered by the electrode array. Rest periods are important during extended treatment periods. The present invention permits treatment to be stopped for a selected interval of time to provide a rest period. The array of electrodes can be a 2 by 2 or 4 by 4 electrode array forming a square, for example, a rectangle of 2 by 4 or 4 by 8 electrodes, or any other configuration desired.

In accordance with another aspect of the present invention, a device is provided for applying a controlled electronic pulse to the skin of a patient. The device includes a pulse generator for generating the pulse, a control for controlling the pulse generator and a probe for transmitting the pulse to the skin of the patient. The probe has an array of electrodes, adjacent electrodes being of opposite polarities. A circuit is provided to measure the current delivered through the electrodes, or an enhanced circuit can be provided to measure the current individually through each of the electrodes. The circuit is thus capable of determining active sites (ie low impedance sites inducing higher current flow) for treatment on the patient. When a probe uses a two wire system, where all electrodes of a given polarity are connected to a common conductor, the current can be measured with the probe on a first site of the patient and measured again after the probe has been moved to a second site to determine which site is more active. If the probe is capable of measuring current flow through individual electrodes, the active sites on the patient's skin covered by the probe can be located without needing to move the probe by evaluating which electrodes draw the most current. In accordance with another aspect of the present invention, orientation of multiple electrode probes are sensed by the instrument based on an orientation marker on the probe array. The probe provides a means to communicate the relative current supplied to each electrode without the need for an electrical connection to each electrode between the device and the probe.

The device can further have a graphic display to illustrate the active sites by showing the variation in impedance as a probe is moved over the skin of the patient or, when individual electrode currents can be measured, by displaying the area under the probe that is most active. In an array of electrodes applied in a fixed position, when individual electrode currents can be measured, the probe can remain in a fixed position on the patient, ie not be moved, and the display can illustrate the area of the skin under the fixed probe that is most active.

When the device is capable of measuring the individual currents through each electrode in a probe, the device would display the relative current flow, or relative activity on a display in a manner corresponding to the particular electrode distribution on the particular probe to inform the user where the active area is actually located under the probe.

In accordance with another aspect of the present invention, LEDs can be positioned between the electrodes to provide light stimulation. The light stimulation is believed to supplement neuro-stimulation.

In accordance with another aspect of the present invention, a central power and control unit is provided to generate a pulse train. At least one patient engaging device is connected to the control unit to direct the pulse train to a plurality of electrodes on the patent engaging device that are in contact with the patient. The patient engaging device can be an arm, knee, elbow or leg cuff, for example. The control unit adjusts the pulse train conditions in response to feedback from the patient, including both passive feedback such as skin impedance, and active feedback from the patient. For example, a series of lights can be displayed on the control unit to inform the patient of the level of treatment and the patient can provide input as to the desirable level.

In accordance with another aspect of the present invention, the control unit can include a circuit to provide alternate pulses to a first patient engaging device and the intervening pulse to a second patient engaging device such that multiple patients can be treated by the same control unit. Use of a control unit separate from the patient engaging device permits the unit to be connected to power at the mains so that battery life or power constraints are not an issue.

In accordance with another aspect of the present invention, the control unit can be programmed to automatically undertake a predetermined analysis and treatment regimen to treat the patient. This eliminates the requirement to have trained staff present during the course of the treatment, freeing resources for other tasks and reducing cost.

In accordance with another aspect of the present invention, the control unit can be in communication through a packet type data exchange system such as the Internet with a central control facility directing the treatment regimen of the control unit through the data exchange system. The control unit can provide feedback to the central control facility to alter the treatment regimen based on the measured tissue impedance of the patient. The control unit can provide initial skin impedance data to the central control facility, with the central control facility evaluating the initial data and transmitting the recommended treatment regimen to the control unit for treating the patient. Dual control by the local control unit and remote central control facility is possible, perhaps with the local control unit providing coarse adjustments and the remote central control facility finer adjustments to the treatment regimen.

In accordance with another aspect of the present invention, the patient engaging device can be a back treatment device with electrodes positioned down the spine of the patient and on either side of the spine of the patient. The control unit can be programmed to apply a pulse train to selected ones of the electrodes in a predetermined pattern to treat the back and neck. The control unit will have the ability to display a representation of the back or neck and the position of the electrodes on it. The probe can be positioned at a known or identified location on the back or neck so that the display on the device represents the precise location of the electrodes on the back or neck. The control unit will first identify the active areas on the back or neck by measuring impedance down the back and then treat the active areas.

In accordance with another aspect of the present invention, a cold laser can be used in combination with the control unit to treat the patient.

In accordance with another aspect of the present invention, the use of multiple electrodes provides the possibility of different patterns of pulses for the different electrodes, being variable in amplitude, duration and strength, for example, thus treating different areas of the patient with different patterns. For example, first and second electrode pairs could each be pulsed for 20 seconds, or the first electrode pair for 30 seconds and the second electrode pair for 5 seconds. As another example, if 20 electrode pairs are used, electrode pairs 1, 4, 8 and 11 could be operated at higher voltages. Stimulation differences can be accomplished by multiplexing a single pulse generator or multiple pulse generators.

In accordance with another aspect of the present invention, the electrodes can be placed on opposite sides of a limb.

In accordance with another aspect of the present invention, a hand held device can be initially employed to isolate an area for treatment, with subsequent treatment undertaken with an electrode on the device or a multiple electrode probe or pad, preferably a flex array, attached to the device, or by a central control unit and a patient engaging device, such as a fixed probe.

In accordance with another aspect of the present invention, the central control unit generates a pulse train, with alternate pulses used to treat different areas on the patient or even to treat different patients. For example, use of 12 electrodes (forming 6 electrode pairs) could allow six different areas to be treated by directing every sixth pulse to a particular electrode pair. This results in effectively treating all of the areas at the same time, even though, at a given instant of time, only one area is being treated.

In accordance with another aspect of the present invention, a treatment process can be undertaken by determining the area to be treated by patient feedback or by the instrument identifying active areas. That area can be researched and then treated. For example, a pain in the leg could involve areas of the back. If the area of back containing the related area is determined, a number of readings can be taken of the skin impedance at spaced points in this area on the back and this data sent by RF transmission from a hand held unit to a central computer. The central computer will analyze the data and transmit back a course of treatment or treatment protocol. The past records of the patients can be stored in the computer memory so that when the patient comes in for treatment, the central computer can download a recommended treatment protocol to a hand held unit for treating the patient.

In accordance with another aspect of the present invention, a patient engaging device can be used which has multiple electrode pairs in contact with an area of the body, for example a knee cuff with electrode pairs in contact with the front and sides of the knee. The treatment can begin with an equal strength pulse delivered to each electrode pair. The pulses can be below the level of perception or increased in strength gradually until the patient senses the pulses. Then a diagnostic procedure is undertaken at the treatment points to determine the skin impedance at each of the points. Those points that show the greatest abnormal readings can then be treated. This would be expected to be faster than treatment by a simple handheld unit as multiple areas can be diagnosed and treated at the same time. In addition, the ability to treat multiple points at the same time would be expected to provide an additive treatment effect.

The patient engaging device can have alternating electrodes and LED's to simultaneously treat the patient by electrical pulse and light treatments.

BRIEF DESCRIPTION OF THE DRAWINGS

For a more complete understanding of the present invention and the advantages thereof, reference is now made to the following Detailed Description taken in conjunction with the accompanying drawings, in which:

FIG. 15 is a view of the display and selection buttons on a device with a different menu to select a preset treatment protocol from;

DETAILED DESCRIPTION

Figure 1:
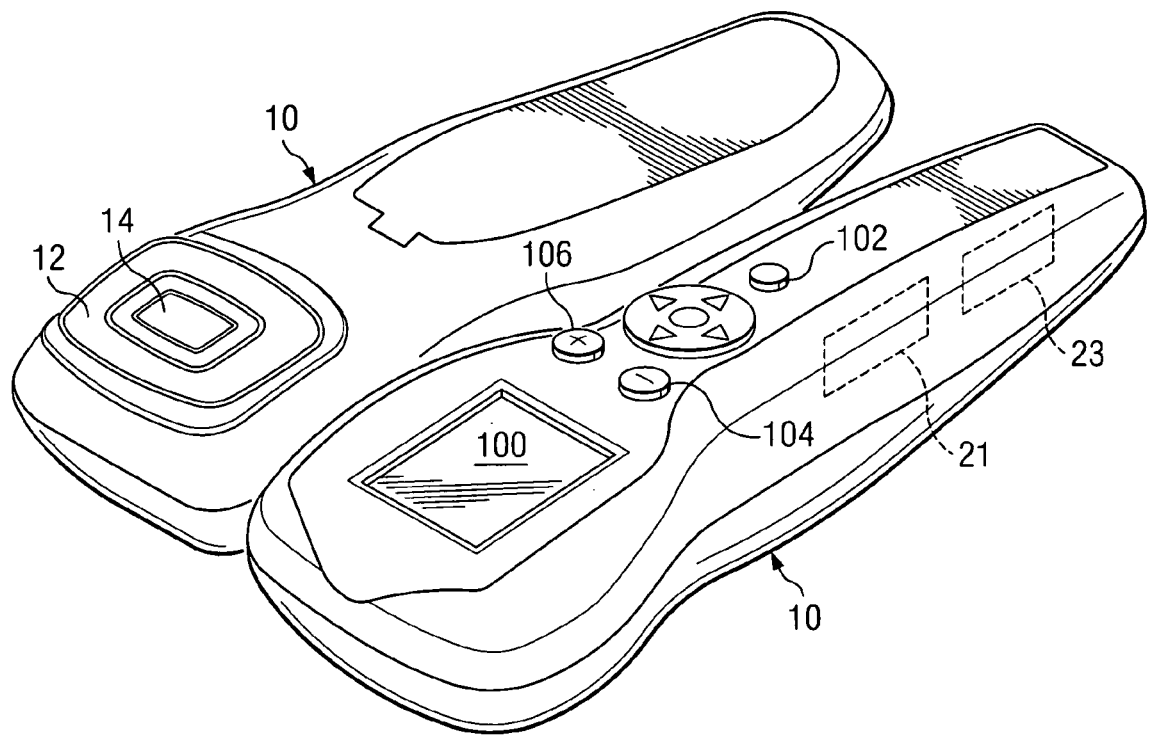
FIG. 1 is a perspective view of a device forming a first embodiment of the present invention, the Professional Sport device.
Figure 2:
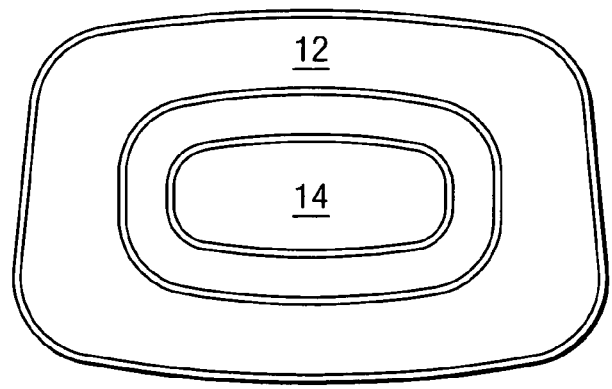
FIG. 2 is a plan view of a pair of electrodes on the device.

With reference now to the accompanying drawings, wherein like or corresponding parts are designated by the same reference numerals, FIG. 1 illustrates a non-invasive neuro stimulation Professional Sports device 10 that incorporates certain features of the present invention. Device 10 has two electrodes 12 and 14 mounted integrally therein, forming an electrode pair, sized and shaped for ready contact with the skin of the patient to treat the patient. Device 10 can also be used with various probes, such as probes 16, 130, 150, 170, 180, 190, 200 and 220 described hereinafter, that plug into a suitable socket in device 10. Each of these probes has electrodes as well. If a probe is attached to device 10, the integral electrodes 12 and 14 are deactivated and the signals that would be sent to electrodes 12 and 14 are instead delivered to the electrodes in the probe.

Figure 3:
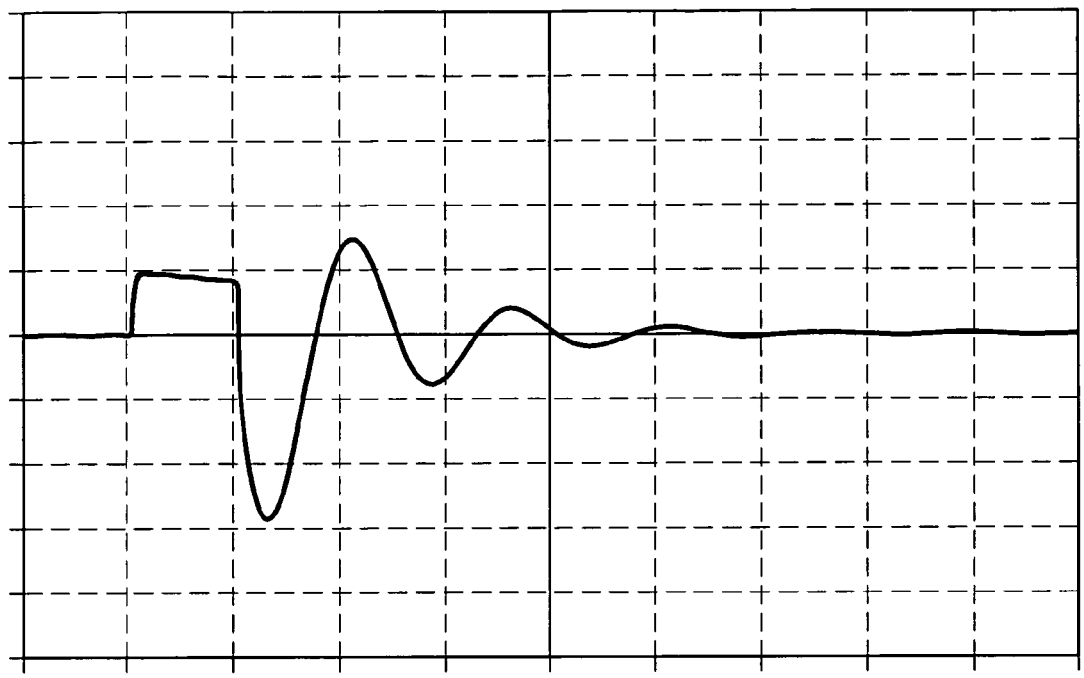
FIG. 3 is a graph of a typical output pulse or spike.

Circuits within the device 10 provide a series of sharp voltage pulses to the electrodes that exhibit a naturally damped ringing oscillation. The output is typically generated by stimulating a transformer coil within the device connected between the output electrodes with a single digital current pulse. The result is an inductive flywheel effect that causes a sharp transient response in the opposite polarity to the applied digital stimulus and with much greater amplitude. The transient response then undergoes classical electronic "ringing", i.e. a naturally damped electronic oscillation as seen in FIG. 3.

For example, the autotransformer may be excited by a negative going electronic impulse of duration 10-12 microseconds, resulting in an unloaded damped oscillatory output, pulse or spike at the electrodes 12 and 14 with an initial peak voltage of 200 volts and a natural oscillation frequency of about 45 K Hz that damps out within a period of approximately 300 microseconds. Circuits in the device 10 allow the addition of loading and damping onto the basic excitation to alter the output characteristics in addition to the natural variation in resistive and capacitive loading represented by the skin and body of the patient being treated. These outputs or pulses are then repeated at predetermined intervals, i.e. repeated at a desired frequency, say 60 outputs per second.

The duration of the exciting impulse into the transformer can be changed to modify the amplitude of the output or pulse at the electrodes 12 and 14. For example, the duration of the input impulse may be selected from within a range of about 10 microseconds to about 500 microseconds.

The device 10 is also capable of varying the intervals between outputs or pulses in a predetermined manner. Besides the uniform interval option noted above, the intervals between successive pulses can be continuously varied, say ranging from 8 milliseconds to 30 milliseconds between pulses over the total period of treatment, say 7 seconds.

Figure 4:
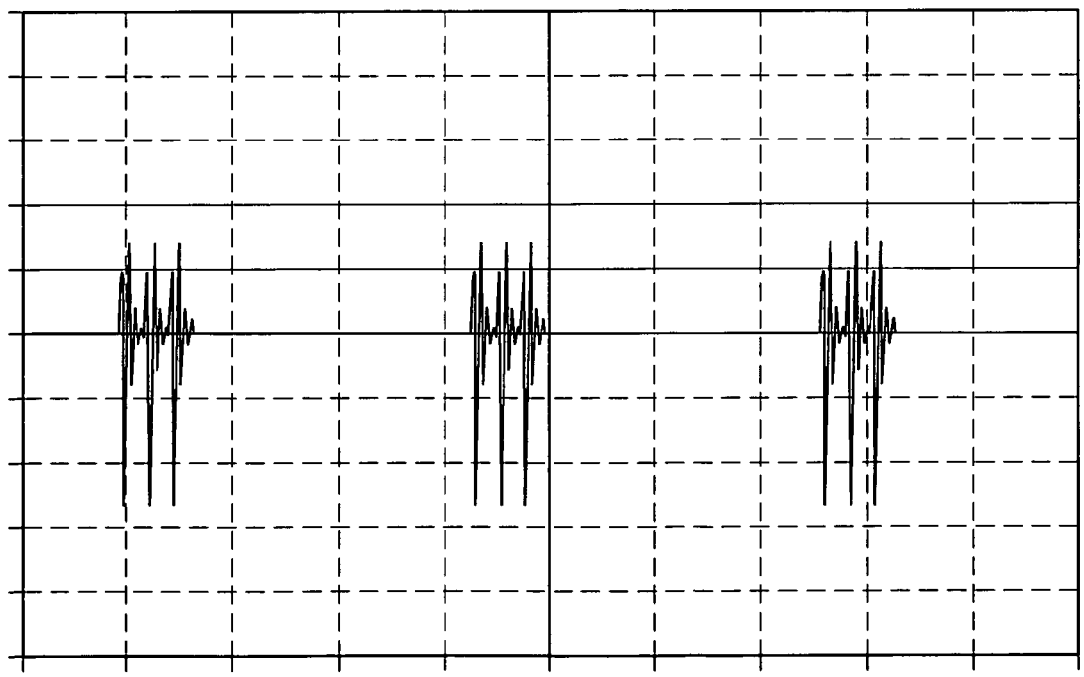
FIG. 4 is a graph of a typical train of output pulses.

Another variation is to have a train of pulses, for example three, in quick succession, as seen in FIG. 4, followed at an interval by another train of pulses in quick succession, with the intervals between the trains of pulses continuously varied as above. Within this variation, it is also possible at the same time to vary the interval between each pulse in the train. For example the interval between each pulse in the train can vary from about 200 microseconds to about 2.0 milliseconds.

The train of pulses noted above can include one or more pulses. Typically, device 10 can provide between one to eight pulses in a given train. The number of pulses in the train is referred to as the intensity. As noted, the interval between each pulse in the train can be varied, typically from about 200 microseconds to about 2.0 milliseconds.

The device 10 also has circuits to determine the electrical characteristics of the output when the device is in contact with the skin and compare the output to that of the output generated when the device 10 is not in contact with the skin to evaluate conditions of the skin and body of the patient. These characteristics include the resistance and capacitance of the patient's skin and body. These characteristics are sampled continuously as the patient is treated as they vary in the course of the treatment, at least in the early stages of the treatment. An observation of limited variation in the characteristics after an interval of treatment can be used as a signal to stop the treatment, indicating the treatment is completed.

In addition to the aspects of device 10 discussed above, the device 10 includes additional inventive features. The device 10 can be connected to a plurality of pairs of electrodes mounted in a patent engaging device or probe 16 for contact with the patient. The patient engaging device 16 can be an arm, knee, elbow or leg cuff, for example. The device 10 adjusts the pulse train conditions in response to feedback from the patient, including both passive feedback such as skin impedance, and active feedback from the patient. For example, a series of lights could be displayed on the device 10 to inform the patient of the level of treatment and the patient can provide input as to the desirable level.

Figure 5:
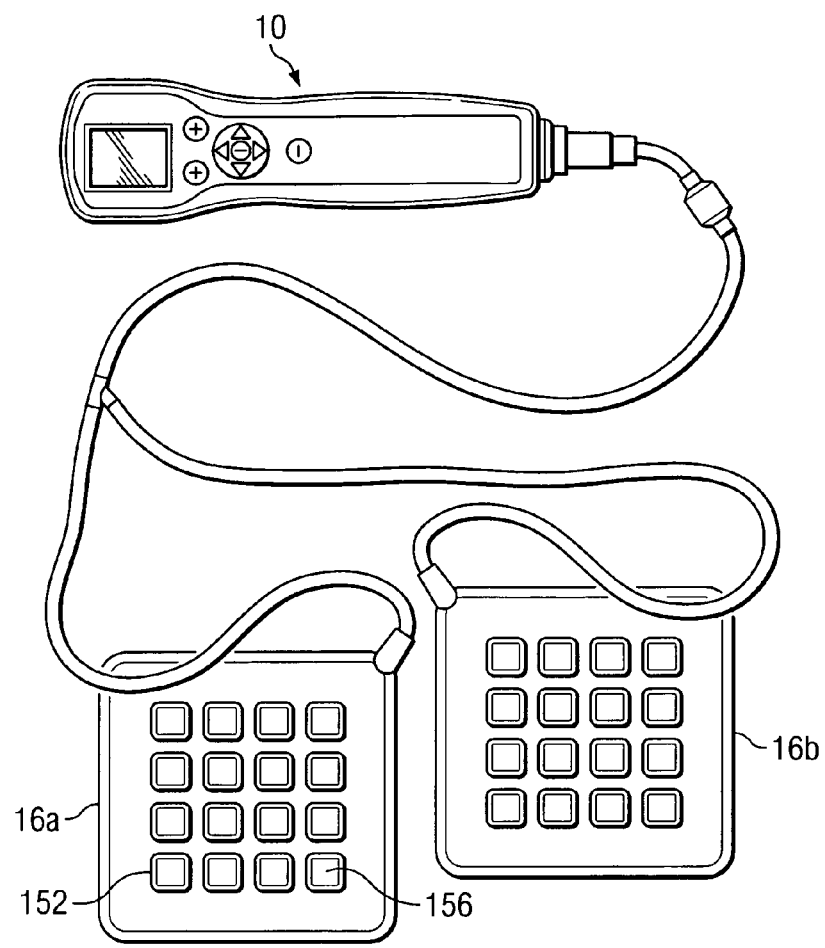
FIG. 5 is an illustration of a device connected to a patient engaging device.

As seen in FIG. 5, the device 10 can include a circuit to provide alternate pulses to a first patient engaging device or probe 16a and the intervening pulse to a second patient engaging device or probe 16b such that multiple patients can be treated by the same device 10. Use of a device 10 separate from the patient engaging device 16 permits the device 10 to be connected to power at the mains so that battery life or power constraints are not an issue.

The device 10 can be programmed to automatically undertake a predetermined treatment regimen or preset treatment protocol to treat the patient. This eliminates the requirement to have trained staff present during the course of the treatment, freeing resources for other tasks and reducing cost.

Figure 6:
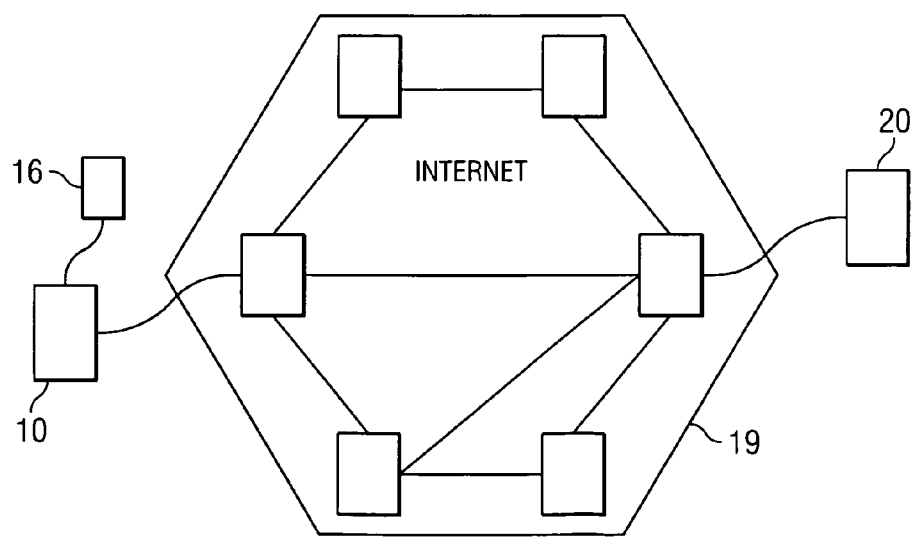
FIG. 6 is an illustration of a system using a device, a central control facility and communication there between by the Internet.

As seen in FIG. 6, the device 10 can be in communication through a packet type data exchange system 19, such as the Internet, with a central control facility 20 directing the treatment regimen of the device 10 through the data exchange system 19. The device 10 can provide feedback to the central control facility 20 to alter the treatment regimen based on the patient feedback. The patient can provide initial symptoms to the central control facility 20, with the central control facility 20 evaluating the initial symptoms and transmitting the recommended treatment regimen to the device 10 for treating the patient. The device 10 can also measure the skin condition of the patient in the area to be treated, transmit this data to the central control facility 20 and receive in return a recommended treatment regimen from the central control facility 20 based on the skin condition. Dual control by the local device 10 and remote central control facility 20 is possible, perhaps with the local device 10 providing coarse adjustments and the remote central control facility 20 providing finer adjustments to the treatment regimen.

Figure 7:
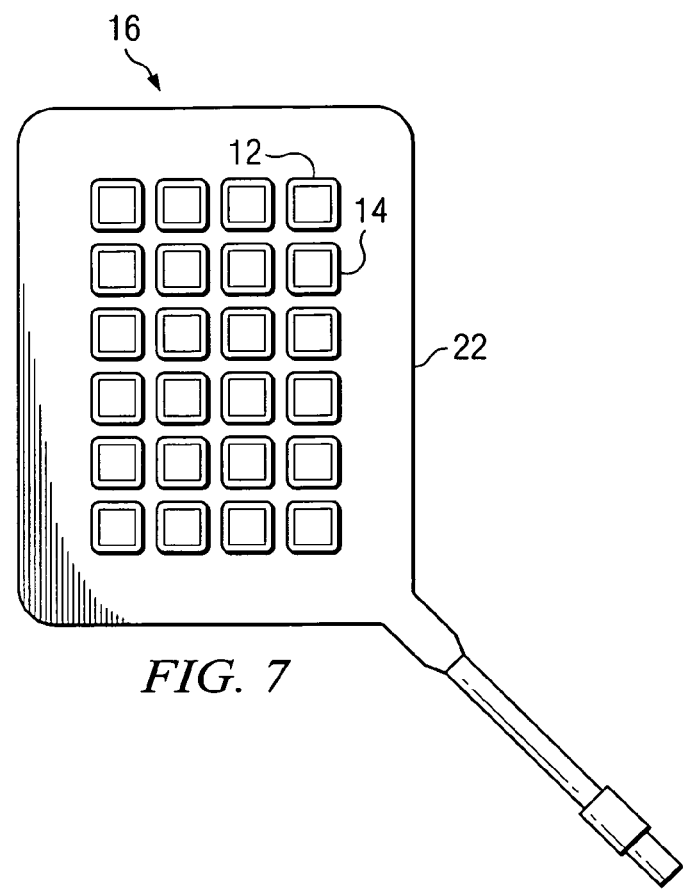
FIG. 7 is a multielectrode patient engaging device such as for treatment of the back.

The patient engaging device or probe 16 can be a back or neck treatment device 22 as seen in FIG. 7, with electrode pairs 12 and 14 positioned down the length of the device 16 to provide a series of contact areas on the back or neck of the patient and on either side of the spine of the patient. The device 10 can be programmed to apply a pulse train to selected ones of the electrodes in a predetermined pattern to treat the back or neck.

Figure 8:
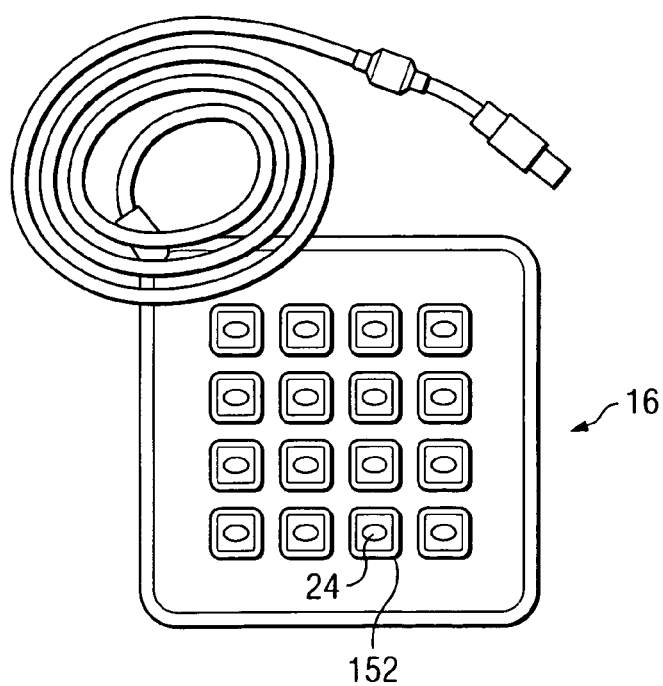
FIG. 8 is an illustration of use of the device with a cold laser.
Figure 9:
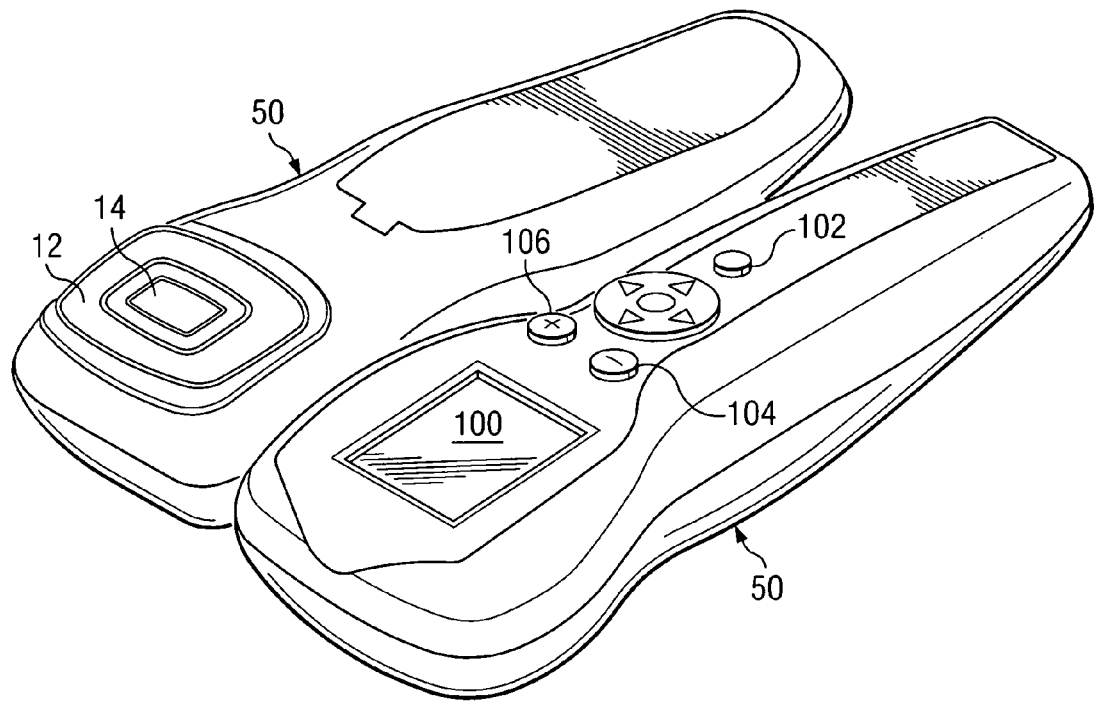
FIG. 9 is a device intended for professional use.

A photonics treatment can be integrated with the electrodynamic pulse treatment provided by a device such as device 10. For example, a cold laser 24 can be used in combination with the device 10 and probe 16 to treat the patient as seen in FIG. 8. Light emitting diodes (LEDs) can also be used to provide the photonics treatment. Cold laser 24, or LEDs 24 can be centered in the electrodes 152, as seen in FIG. 8. When using LEDs, the preferred wavelengths are 635 to 660 nm (visible red) or 800 to 900 nm (near IR). The photonics treatment can be used to two purposes. The first purpose is energetic, providing perhaps 4 to 8 Joules/cm$^2$ to activate ATP mitochondria. The second purpose is for information. The body responds to the application of light, and the response can be measured to determine body conditions for treatment.

The photonics and electrodynamic treatments can occur simultaneously. The treatments can be at the same frequency of application, or at different frequencies. The photonics may be on constantly at a given wavelength and intensity, or can be pulsed. The photonics can be applied randomly or chaotically. The photonics source can be integral with the electrodynamic device, or can be a separate component or plug in attachment such as an LED array. Use of LEDs provide non-coherent light and the ability to vary brightness, intensity, and color. A low level laser (LLL) can also be used. The photonics can provide general potentiation for the electrodynamics, since the body may respond better to the treatment in the presence of the light. The photonics and electrodynamic treatments can constructively interfere, amplifying the effect of both treatments over that possible by each alone.

The photonics and electrodynamic treatments can alternate. For example, the photonics treatment can be applied for 1 second, 5 seconds, etc. and then the electrodynamic treatment for a similar period. The electrodynamic treatment has feedback, as noted, and the feedback can be used to adjust the treatment pattern of the photonics. In fact, the feedback feature of the electrodynamic treatment can be used to provide feedback for the photonics treatment without even treating the patient with the electrodynamic treatment. Thus, a biofeedback of the photonics treatment is provided, with the feedback being near real time so that the pattern, energy and duration of the photonics treatment can be optimized. The LEDs can be pulsed, again controlled by the feedback provided through the electrodynamic treatment. The photonics treatment and feedback control can be alternated, refining the best pattern for treatment.

The use of multiple electrode pairs provides the possibility of different patterns of pulses for the different electrode pairs, being variable in amplitude, duration and strength, for example, thus treating different areas of the patient with different patterns. For example, first and second electrode pairs could each be pulsed for 20 seconds, or the first electrode pair for 30 seconds and the second electrode pair for 5 seconds. As another example, if 20 electrode pairs are used, electrode pairs 1, 4, 8 and 11 could be operated at higher voltages.

The electrode pairs can be placed on opposite sides of a limb.

A hand held device 10 can be initially employed to isolate an area for treatment, with subsequent treatment undertaken with a central control unit 20 that has the same functions as device 10, and perhaps additional functions, interacting with a patient engaging device 16 that is in actual contact with the patient.

The device 10 can generate a pulse train, with alternate pulses used to treat different areas on the patient or even to treat different patients. For example, use of 12 electrode pairs allows six different areas to be treated on the patient by directing every sixth pulse to a particular electrode pair. This results in effectively treating all of the areas at the same time, even though, at a given instant of time, only one area is being treated.

FIGS. 9 and 11-13 illustrates devices 50, 70, 80 and 90 that form additional embodiments of the present invention. Each of the devices 50, 70, 80 and 90 can have the same internal circuits and controls as device 10. Device 10 is a professional device for use in sports. Device 50 is a professional unit, device 70 is designed for home sport use, device 80 is used for home use and device 90 is used for cosmetic applications. These devices 10, 50, 70, 80, and 90 include the advantage of using preset treatment protocols already programmed into the device to allow the user to initiate an entire treatment protocol by simply pushing one button or making a selection off of a menu on a display.

Each of the devices 10-90 have a series of treatment protocols programmed therein by hardware, software or a combination thereof. These protocols can be displayed graphically on a display 100 on the professional devices 10 and 50. These protocols aid and assist the user of the device to quickly find the treatment methodologies that have been found to be most effective in treating a particular medical condition. They also provide guidance for the novice and occasional user of the device. FIGS. 14-17 show various menus that can be displayed on the display 100 of devices 10 that permit the user to choose one of the preset treatment protocols by pushing a select button 102 on the device. The user can scroll through the choices by pushing up and down buttons 104 and 106 until the desired choice is highlighted. The choice is then selected by pushing select button 102, which will initiate the desired protocol. Device 50 would use similar menus. The devices 70, 80 and 90, not having a display 100, will have a number of choices that can be selected by up and down buttons 104 and 106 and initiated by pushing the select button 102. The choice that is chosen for selection will have a lit LED beside the choice. Choices for devices 70 and 80 can include Acute, Chronic, FM Var, Dose and Default, each representing different preset treatment protocols. Choices for device 90 can include Tone, Smooth1 and Smooth2, for example. Devices 70 and 90 have a mode button 105. Pressing the mode button 105 multiple times cycles the device through each mode in turn and then starts at the beginning again. The + button increases the stimulation amplitude. The − button decreases the stimulation amplitude. The lower button is the on/off button.

Figure 14:
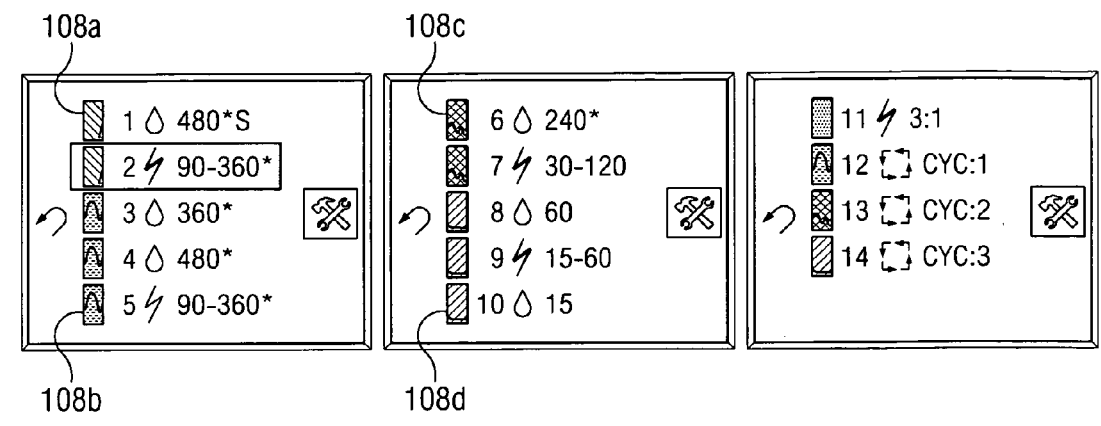
FIG. 14 is a view of the display and selection buttons on a device allowing the user to select from a menu of preset treatment protocols.
Figure 15:
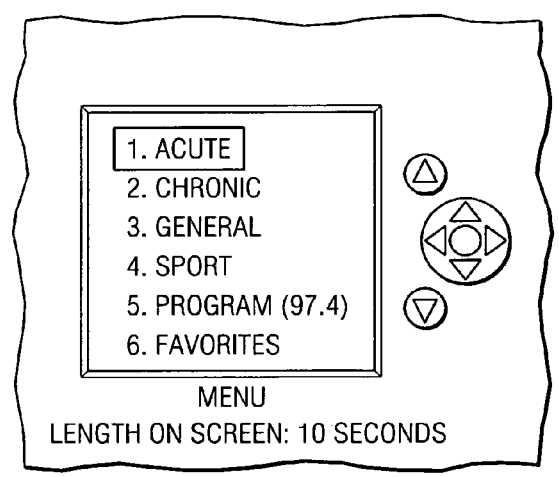
Figure 16:
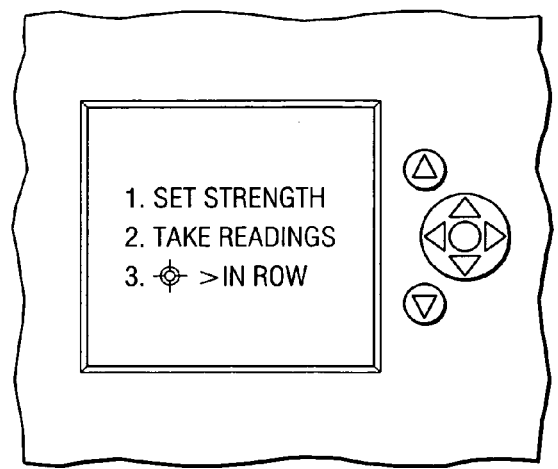
FIG. 16 is a view of the display and selection buttons on a device with a menu to select parameters in the device such as strength.
Figure 17:
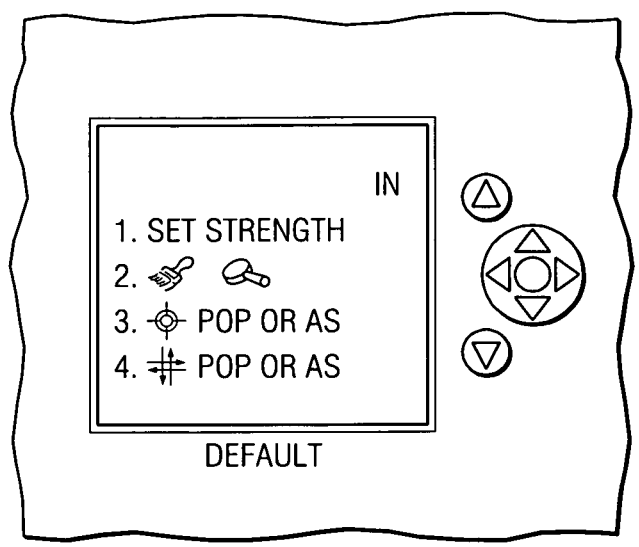
FIG. 17 is a view of the display and selection buttons on a device with a different menu.

For example, as FIG. 14 illustrates, the device 10 may have preset treatments. FIG. 14 shows 14 preset treatments numbered 1-14. Each preset has a portion of the injury curve 108*a-d* shown to the left of the preset number, indicating that preset would be beneficial to treating an injury at the particular stage shown. Preset 1 indicates 480, meaning 480 pulses per second (pps). Preset 2 indicates 90-360, which indicates the pulses swing between 90 to 360 pulses per second. Pulses per second can be delivered in burst, variable or continuous stim patterns. Presets 1, 3, 4 and 6 are burst patterns. Preset 1 is 480 pps with 8 impulses per burst and 60 bursts per second. Preset 3 is 360 pps with 6 impulses per burst and 60 burst per second. Preset 4 is 480 pps with 8 impulses per burst and 60 burst per second with a longer delay between impulses. Preset 6 is 240 pps with 4 impulses per burst and 60 bursts per second. Presets 2, 5, 7 and 9 are variable stim patterns. In these, the patterns will range between the two frequencies listed, the highest and lowest pps in the range. Presets 2 and 5, 90-360 pps, are 3 pulses per burst, variable between 30 and 120 bursts per second. Preset 7, 30-120 pps, is variable frequency between 30 and 120 pps. Preset 9, 15-60 pps, is variable frequency between 15 and 60 pps. Presets 8 and 10 are continuous stim patterns with a consistent frequency pulsed waveform. Preset 8 is 60 pps and preset 10 is 15 pps. Preset 11 is 3:1 modulation with 121 pps which modulates 3 seconds on and 1 second on. Presets 12, 13 and 14 are cycle patterns. This pattern uses a series of preset patterns in a 5 minute period. The cycle will repeat until the maximum treatment time of 10 minutes has been reached. Preset 12 performs preset 5 for 2 minutes, preset 7 for two minutes and preset 5 for 1 minute. Preset 13 performs preset 5 for 1 minute, preset 6 for 2 minutes, preset 7 for 1 minute and preset 11 for 1 minute. Preset 14 performs preset 7 for 2 minutes, preset 9 for 2 minutes and preset 10 for 1 minute. Clearly, presets differing from those shown in FIG. 14 and described above can be used and developed as appropriate. The device allows one of these presets to be selected directly, or the operator can click on one of the bars 108*a-d*, which can initiate one of the preset treatments for that stage of injury treatment or bring up another menu allowing a choice of the present treatments recommended for that stage. Other presets can be PS1, PS2, PS3, PS10, PS11, UD1 and UD2. PS would represent a preset treatment programmed or designed into the device by the manufacturer. UD would represent a preset treatment defined by the user, perhaps representing a treatment protocol particularly effective for a chronic pain or commonly treated condition. By using a preset treatment protocol, the user is freed from having to make the many individual settings for a treatment, such as the frequency of the pulses, the modulation of the pulses, the number of pulses in a packet, etc. The individual settings can be time consuming and confusing to a novice or occasional user.

Figure 18:
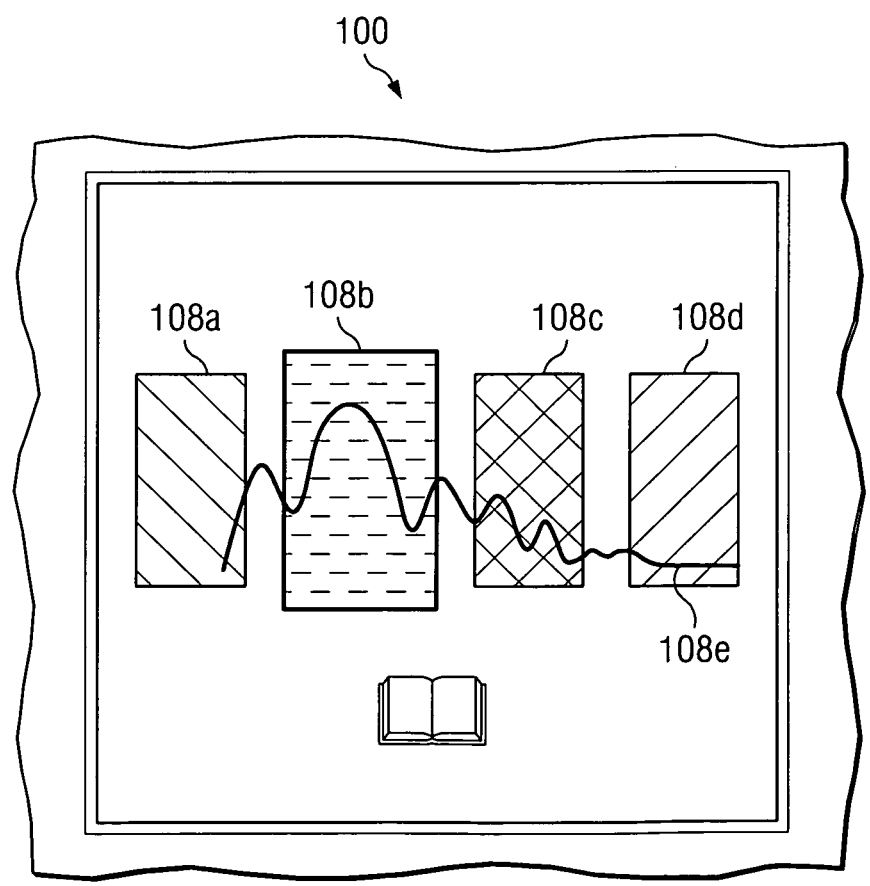
FIG. 18 is a view of the display and selection buttons on a device with five stages of injury recovery represented on the display as five adjacent vertical bars, allowing a preset treatment protocol appropriate for a specific stage to be implemented by highlighting the specific stage by activating the selection buttons.

It is well recognized in sports injuries that the injury progresses through five separate stages, beginning with pre-inflammation, then proceeding through inflamed, remodel, repair and reform stages, which can sometimes be illustrated as an injury curve. A modified version of these stages is represented on display 100 in FIG. 18 by a bar graph with four discrete vertical bars 108*a-d* of different colors with the repair and reform stages combined in the four bar 108*d*. More particularly, bar 108*a* represents acute onset-initial occurrence as systems develop. Bar 108*b* represents acute inflamed-peak of injury symptoms. Bar 108*c* is repair-symptoms begin to improve. Bar 108*d* is chronic-conditions that persist past expected recovery time. The injury curve 108*e* is shown progressing through each of the four bars representing the four stages of the modified injury curve. The user of the devices 10 and 50 can highlight one of the bars by manipulating up and down buttons 104 and 106 until the bar representing the desired stage of the sports injury to be treated is highlighted. Pressing the select button 102 then initiates a preset treatment specifically designed for effective treatment of that stage of the injury. This interactive display allows an athletic trainer or physical therapist to treat an injury with the device with very little instruction.

Other preset treatments can be provided to treat conditions of chronic or acute pain, inflammation, and the like. The preset treatment for each condition would be designed to best treat that condition. In devices 10 and 50, these preset treatments can be selected off a menu by pressing the appropriate buttons 102, 104 and 106. In devices 70 and 80, the buttons 102, 104 and 106 can be pressed to light the LED beside the condition to be treated which initiates the preset treatment for that condition.

The devices 10-90 will be provided with a communication port that will allow the devices to be updated as needed when new treatment protocols are developed. The updates can be made by connecting the device to a packet type data exchange system such as the Internet, for example.

It is generally understood that the most effective treatment by devices 10-90 will occur in areas where the skin impedance is the lowest, ie the capacitance the greatest. These are referred to as the active areas. These areas are seen to be gates to effective body treatment and a goal is to stimulate the tissue in these areas. The devices 10-90 are capable of measuring the skin impedance and communicating the measured value, at least in a relative sense, to the user audibly, visually or both. Devices 10 and 50 can use display 100 for this purpose as well as sound. Devices 70, 80 and 90 do not have displays, but do have a sound producing device such as a speaker so that an audio signal can used, perhaps supplemented by a visual indication using LEDs on the devices.

Figure 21:
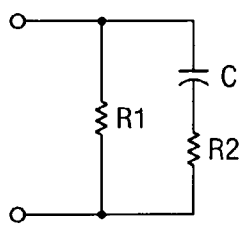
FIG. 21 is an electrical circuit equivalent to the electrical characteristics of the human skin and underlying tissue.
Figure 22:
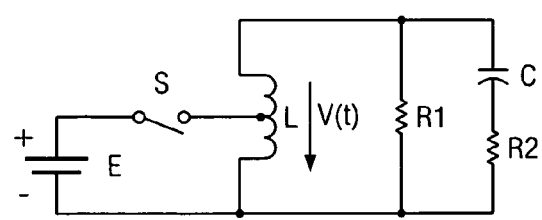
FIG. 22 is an electrical circuit to apply a pulse to the tissue.
Figure 23:
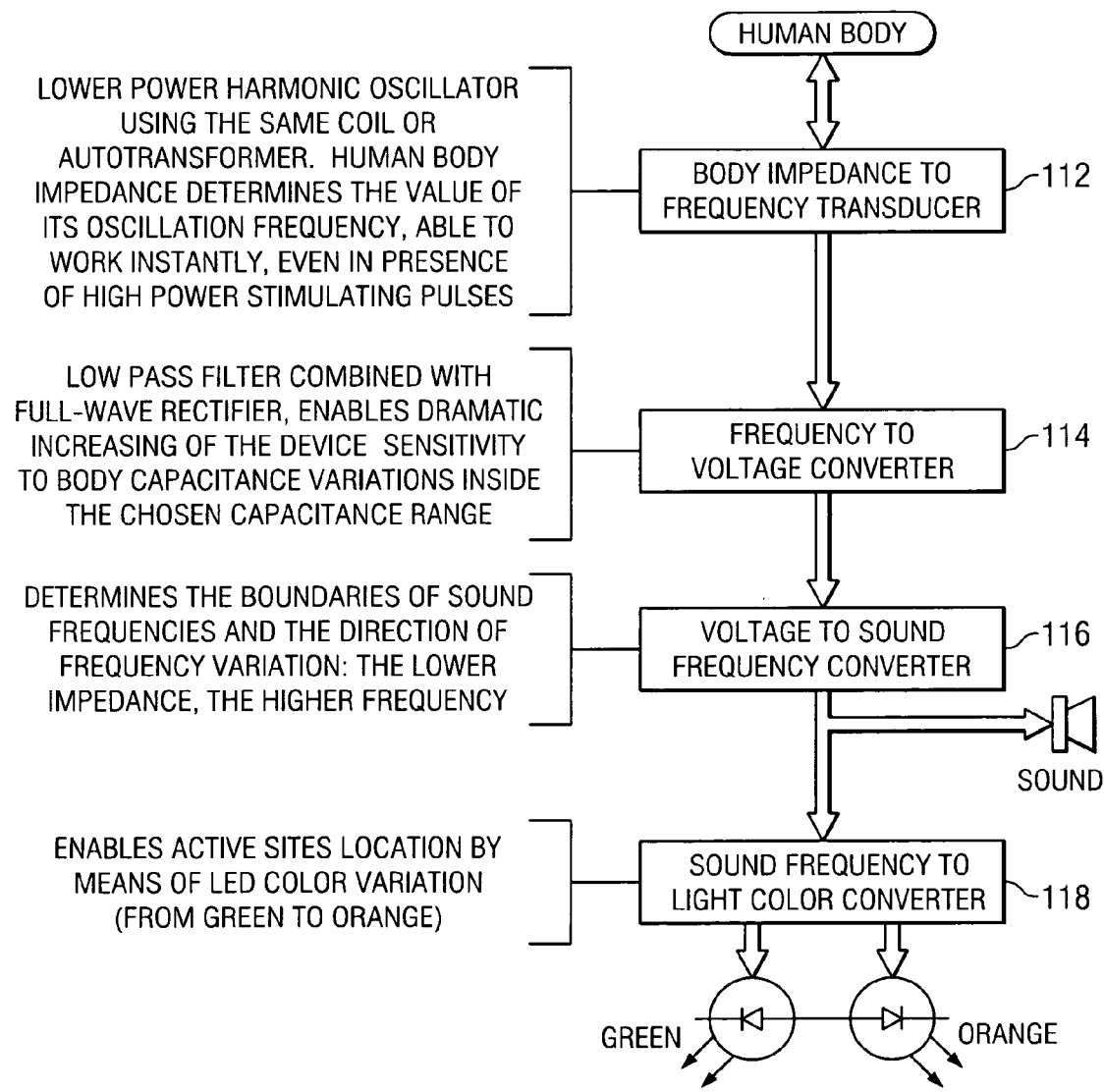
FIG. 23 is a flow chart showing the steps of measuring skin impedance and presenting a representation of the impedance measured as an audio or visual signal varying in frequency or strength depending on the relative impedance measured.
Figure 24:
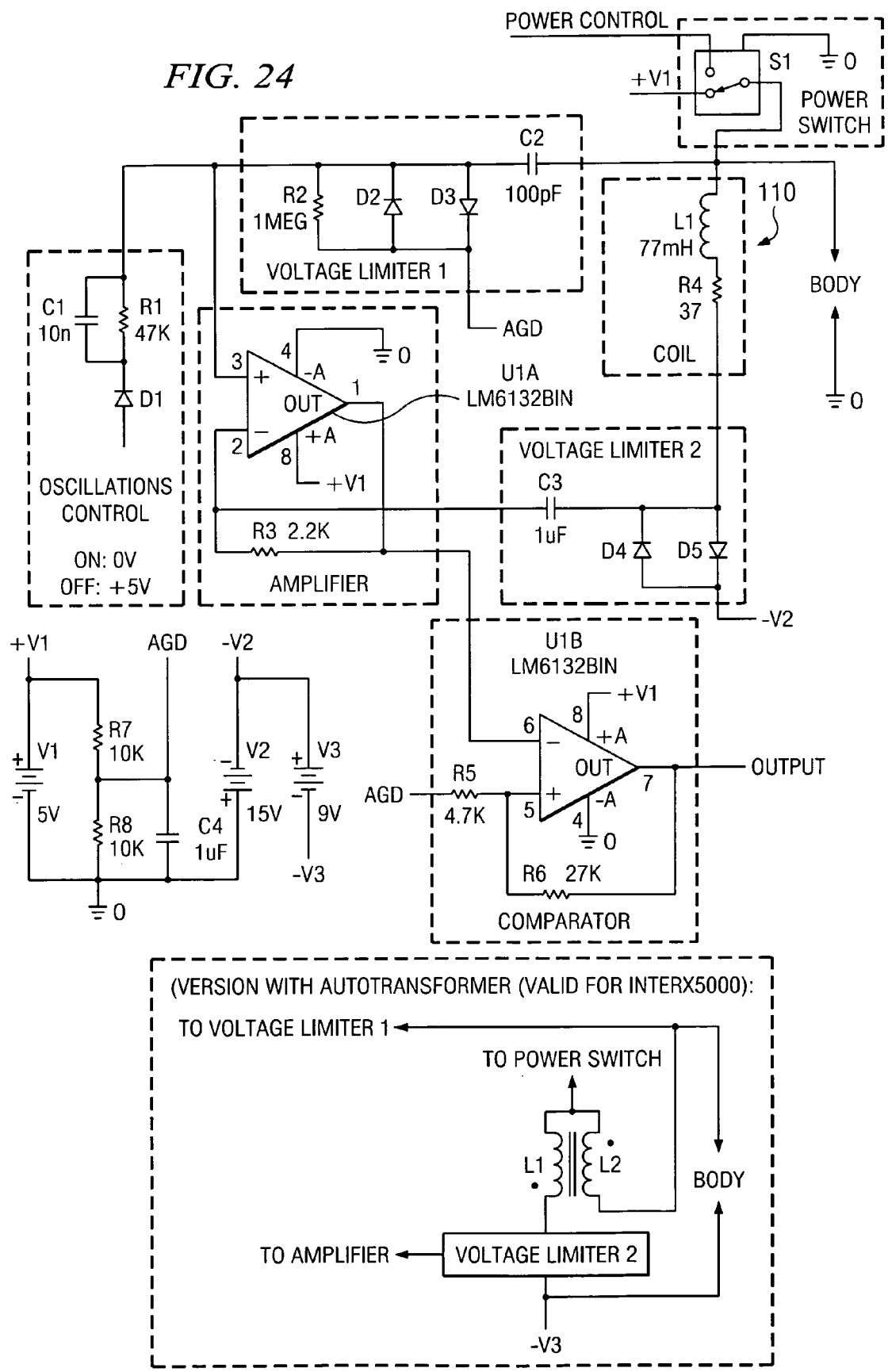
FIG. 24 is a circuit suitable for measuring skin impedance and converting the measured value to a frequency used to generate an audio or visual indication of relative impedance.
Figure 25:
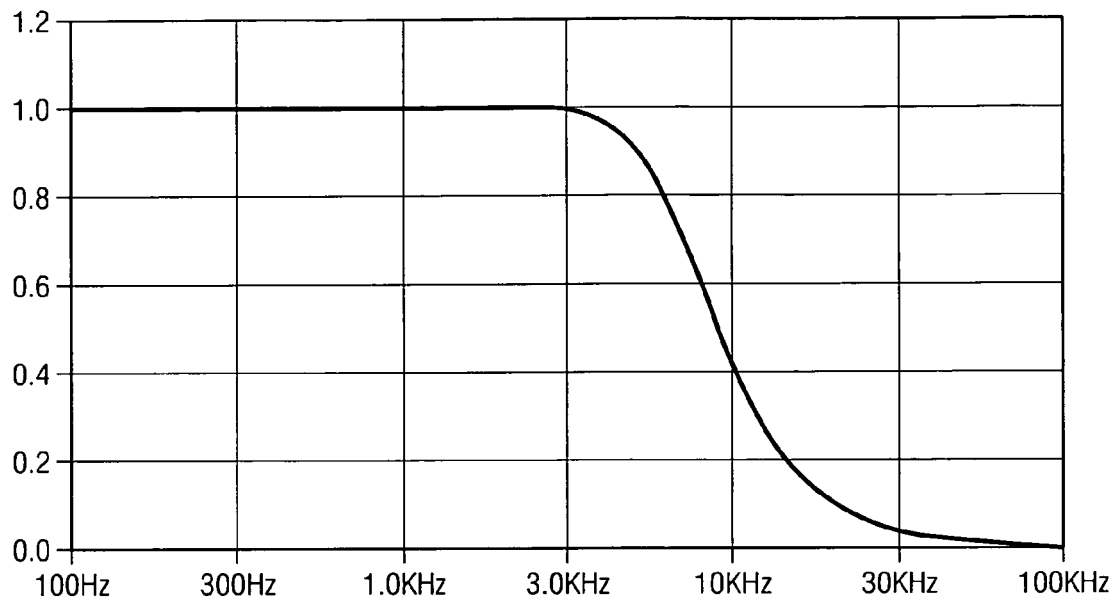
FIG. 25 illustrates low pass filter frequency response to allow the device to compensate for changes in skin impedance as the treatment progresses.

At the present time, the sensing of skin impedance by a device is the indirect result of actual treatment of the patient. As seen in FIG. 21, the body's skin and underlying tissue is represented by an equivalent circuit with two resistors R1 and R2 and a capacitor C. R1 is usually relatively high while R2 is relatively small. FIG. 22 illustrates a typical circuit to apply a pulse to the tissue. When the treatment pulse is applied, the period of the free oscillation of the circuit is measured and used to determine the impedance. As a result, as the user is passing a device over the skin to sense variations in impedance, the patient is actually being treated as well. However, the skin impedance changes during the treatment. Thus, the current method of testing itself alters the results of the test. In contrast, the method of the present invention provides for an accurate survey of the skin before treatment to isolate the active areas.

The present invention allows a user to measure tissue impedance using small amplitude signals that do not treat or change tissue impedance, prior to actual treatment. FIGS. 23-29 illustrate the implementation of one embodiment of the invention. A small amplitude signal, with far less power than a treatment pulse, is generated at the same transformer 110 used to apply the treatment pulse and is applied to the skin at the area being tested. The circuit determines the frequency of oscillation, which is directly related to the skin impedance. This is represented by step 112 in the flow chart to determine the active areas presented in FIG. 23. A frequency to voltage converter 120 illustrated in FIG. 26 converts this oscillation frequency to a voltage signal. This provides a dramatic increase of sensitivity to body capacitance variations. This is represented by step 114 in FIG. 23.

Figure 27:
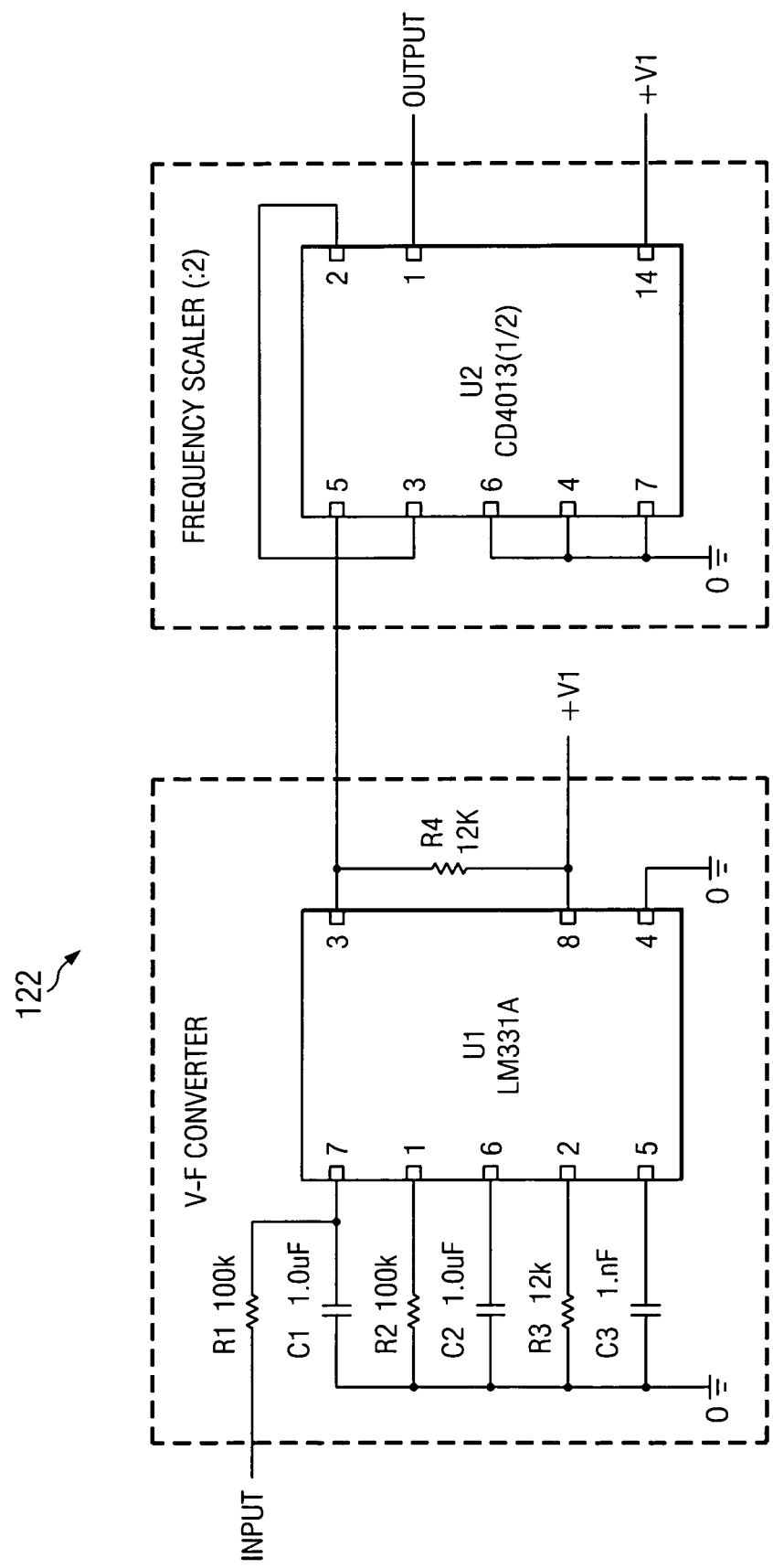
FIG. 27 is a voltage to audio frequency converter that can be used in the device.
Figure 28:
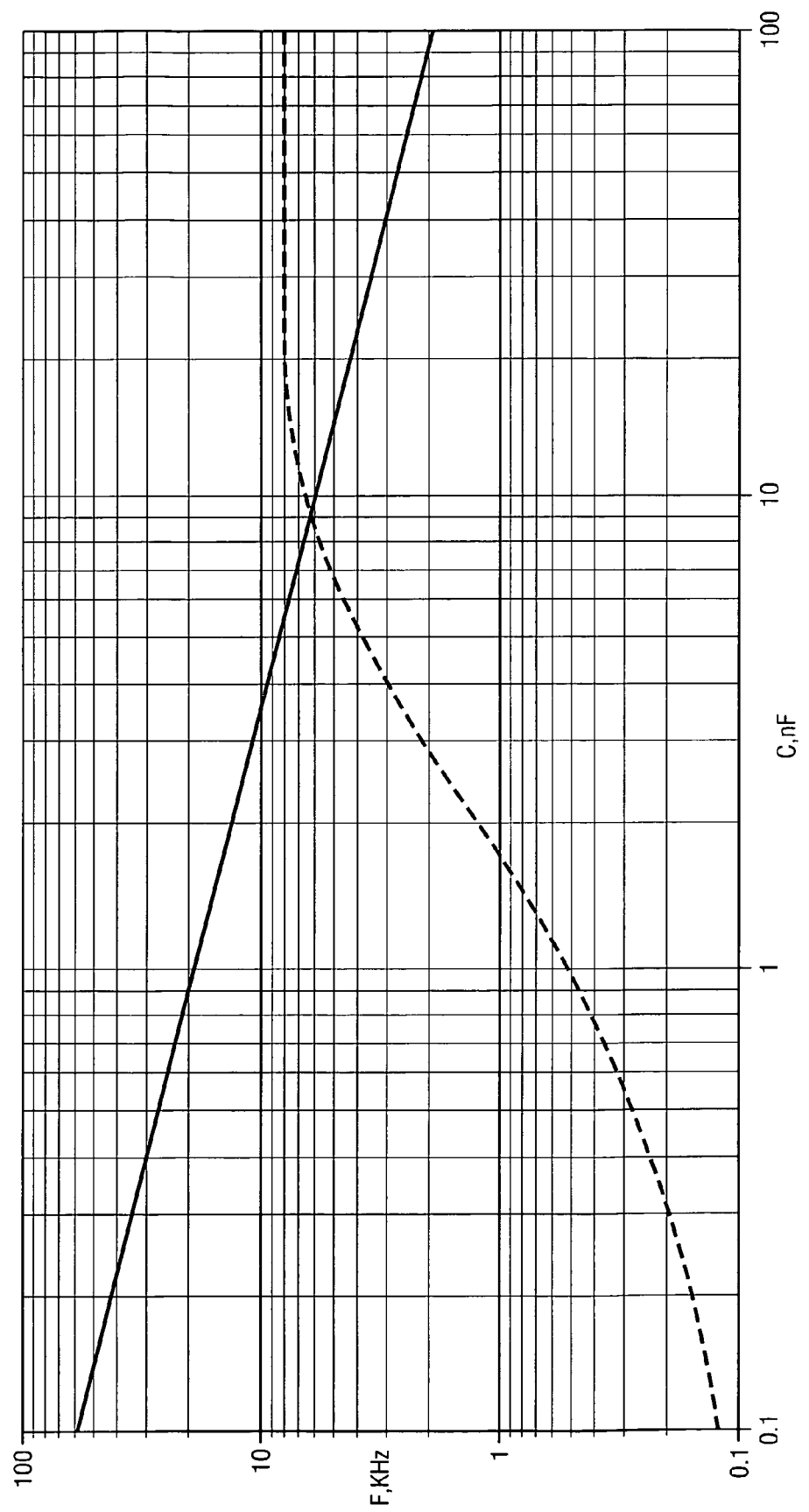
FIG. 28 is a graph of transducer frequency and audio frequency variation in relation to the measured skin impedance suitable for use with the device.

Preferably, the variable voltage representing the skin impedance is then transformed into an audio signal, with the audio frequency related to the skin impedance so that the user can easily find active sites by simply passing the device over the skin and listening for the tone of the audio signal to change to the pitch indicating low impedance. FIG. 27 illustrates a suitable circuit 122 to convert the voltage to an audio signal. One advantage of using an audio signal is that the user need not be constantly removing the device from the skin to read an impedance value on a visual readout. The user need only monitor the audio tone as the device is moved along the skin to find the active areas. This is represented by step 116 in FIG. 23.

Figure 29:
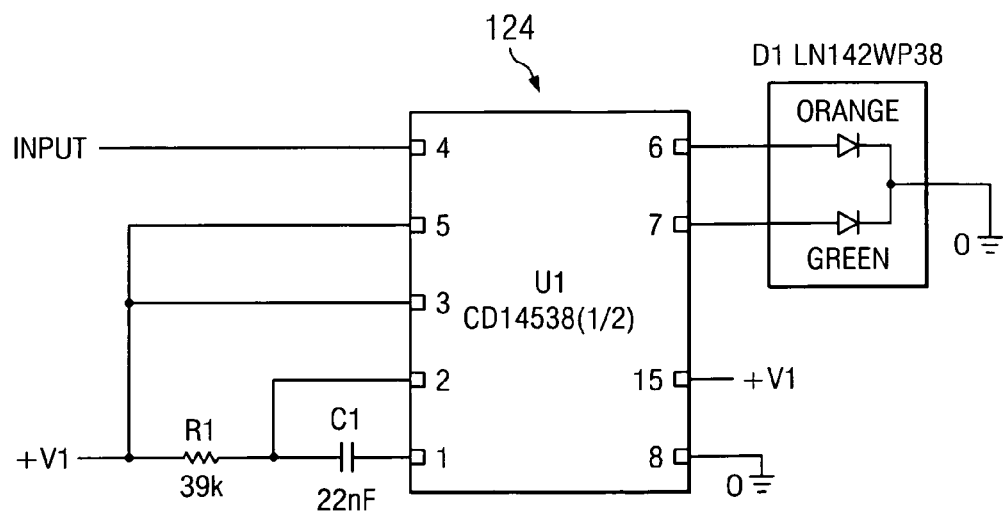
FIG. 29 is a frequency to light color converter circuit that can be used in the device.
Figure 26:
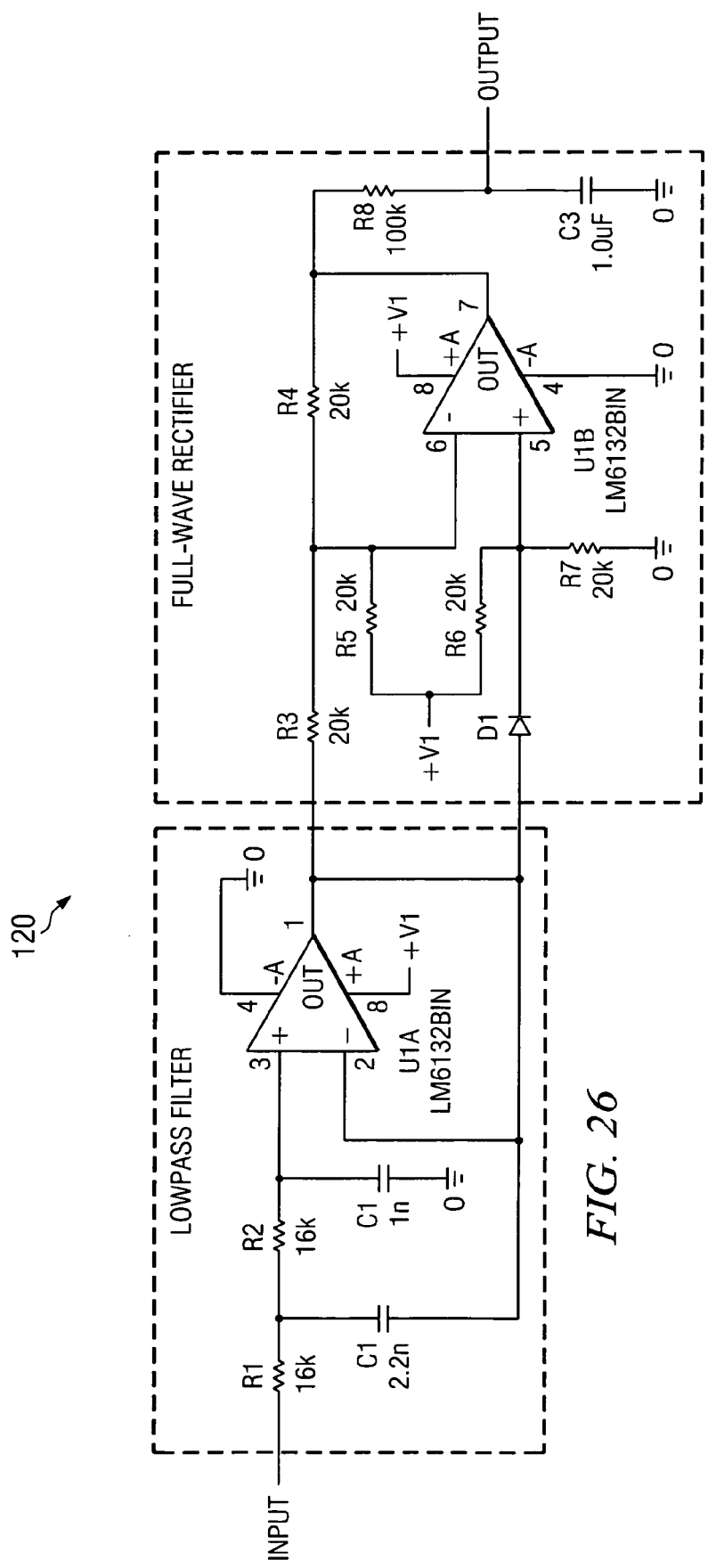
FIG. 26 is a frequency to voltage converter circuit that can be used in the device.
Figure 30:
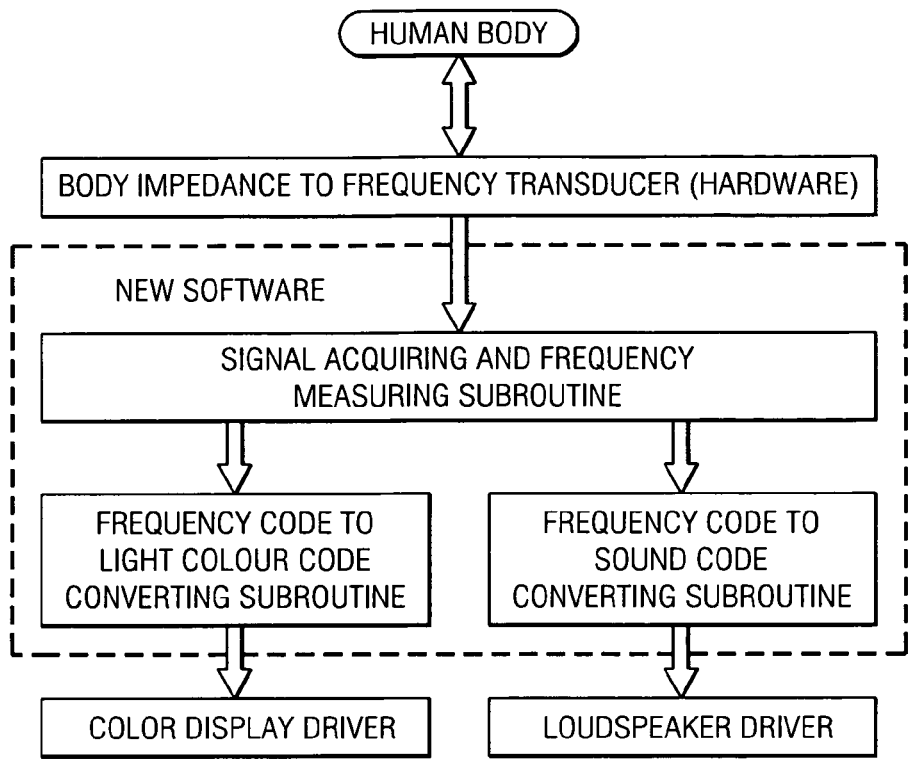
FIG. 30 is a flow chart of software that can be used to implement the task of converting the measured skin impedance to an audio or visual signal representative of the relative impedance.

A visual display can be used to supplement, or replace, the audio signal. This is represented by step 118 in FIG. 23. FIG. 29 illustrates a circuit 124 that will activate orange and green LEDs in response to the impedance measured. When the input signal period is shorter than Tp=R1C1, pin 6 of U1 is in the "on" state, and pin 7 is off, lighting the orange LED only. When the period becomes longer, periodic pulses appear at both pins 6 and 7, lighting the orange and green LEDs alternatively. Relatively equal activation periods of the green and orange LEDs result in a yellow color. When the period reaches a certain length, effectively only the green LED is on. Thus, as the frequency varies, the input signal period varies and the appearance of the LEDs will shift gradually from orange to yellow to green, giving a visual indication of skin impedance. Use of this type of visual display also has the advantage of not needing to constantly remove the device from the skin to read an impedance as well. These functions can be implemented in hardware as shown in the Figures referenced, or in software, as illustrated in FIG. 30. As a result, the impedance of the region to be treated can be quickly evaluated just prior to treatment and the active areas located to enhance the effectiveness of the treatment.

Further, the circuits can have a feature to adjust or scale the audio output range to the particular range of impedances found. For example, the full audio range can be applied equally to variation of impedance that varies over an order of magnitude, or applied to a variation that only differs by a factor of two. The absolute value of skin impedance is not as important as the value of impedance of one area of skin relative another area of skin so as to allow determination of the area of lowest impedance or active area in the overall area to be treated. Such a feature is most likely implemented in software.

More sophisticated circuits such as a phase detector can also be used to isolate the capacitance component from the resistance component of the skin. It is believed the capacitance is more directly related to the effectiveness of treatment so that isolation of the capacitance will lead to more accurate location of the active areas. Resistance can vary with factors unrelated to those useful to treatment evaluation, such as when the patient is sweating or has damp skin, leading to lowered resistance.

Figure 10:
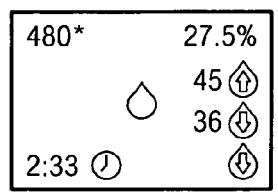
FIG. 10 is illustrates dose tapping/auto stim.
Figure 10:
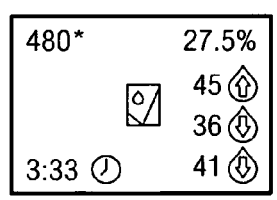
Figure 10:
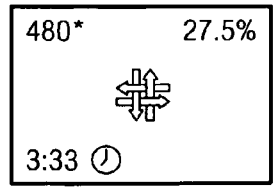
Figure 13:
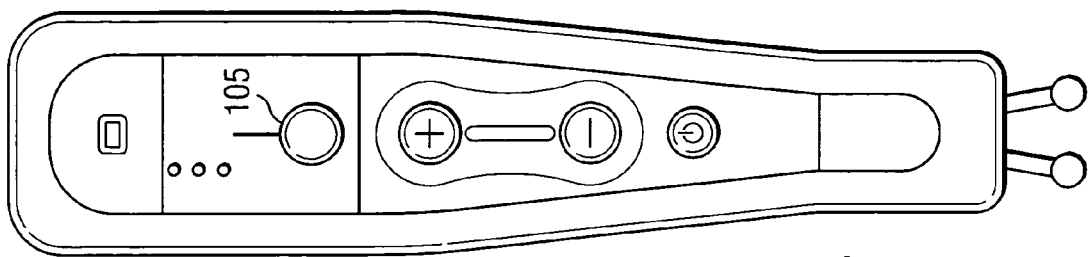
FIG. 13 is a device intended for cosmetic applications.
Figure 12:
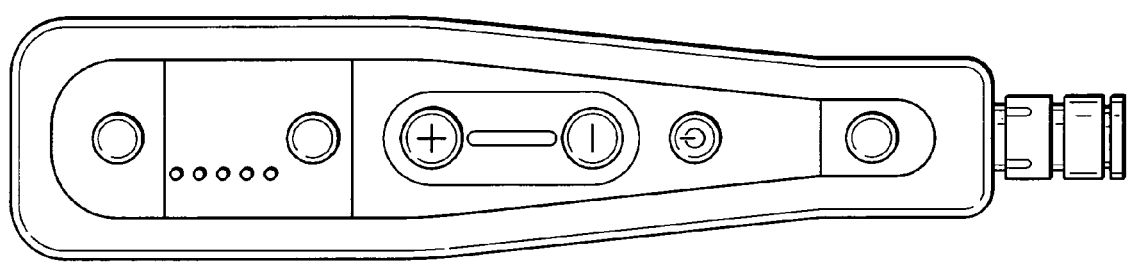
FIG. 12 is a device intended for home use.
Figure 11:
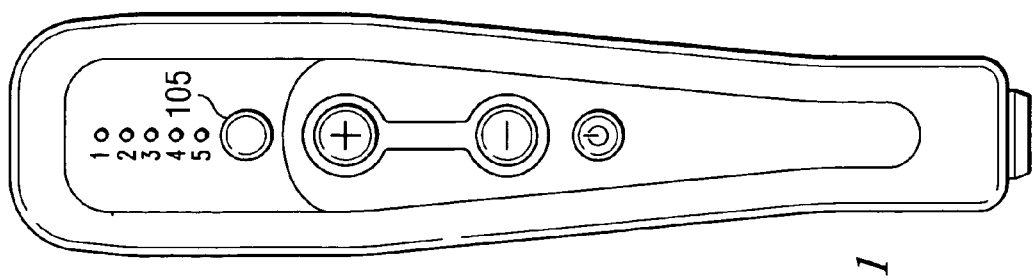
FIG. 11 is a device intended for home sport use.

The devices of the present invention are also capable of automatic dose tapping. Dose tapping is a process of applying a series of treatment pulses while monitoring the tissue impedance response after each treatment. The treatment is applied a sufficient number of times until the tissue response or impedance is optimum. It has been observed that the impedance will change during treatment, but eventually stabilize at a given value. When this stable or optimum value is reached, the treatment is complete. FIG. 10 shows dose tapping/auto stim. The number 480 represents 480 pulses per second. 27.5% represents the intensity relative full intensity. Point stim allows treatment of a single point on the skin and will generate a value of skin impedance. An auto stim is a series of point sitms that occur with a pause between each, say 3 seconds. The peak value measured is displayed on the top right side of the screen in FIG. 10 and any lower values are saved below. The auto stim can be complete when either the sequence of values peaks and then falls twice consecutively or when 8 point stims have been completed.

The devices can also monitor the energy delivered to the patient in each pulse. The analysis of the stimulation signal combined with a software control loop allows software to adjust the stimulation signal so as to deliver a fixed net charge regardless of changes of tissue impedance. This allows stimulation signals to retain more consistent effectiveness as the devices are moved over the skin. For example, as the tissue impedance changes during the course of a treatment, the pulse strength can be varied to maintain the same energy delivered to the patient. Variation of the frequency of the pulse can be employed as well.

The devices can also incorporate software that monitors the response of the tissue and maintains the same level of treatment perceived by the patient, in spite of variations in impedance. The software can increase the amplitude of the pulse, for example, to deliver more actual energy to the patient to maintain the perceived level of treatment the same.

As mentioned previously, the devices can be used with the skin contacting electrodes mounted integrally in the device or with interchangeable patient engaging devices or probes having different electrode configurations. For example, a certain probe may be configured for a certain part of the body, such as the arm, or the back or neck. Alternatively, a probe may be application specific. Software within the device will normalize tissue impedance readings and optimize maximum energy settings based on the probe type. The devices will be able to automatically detect the type of probe used therewith. One technique to achieve this result is to mount a resistor of different value in each type of probe. The device need only measure the value of the resistor to know the type of probe attached.

Figure 31:
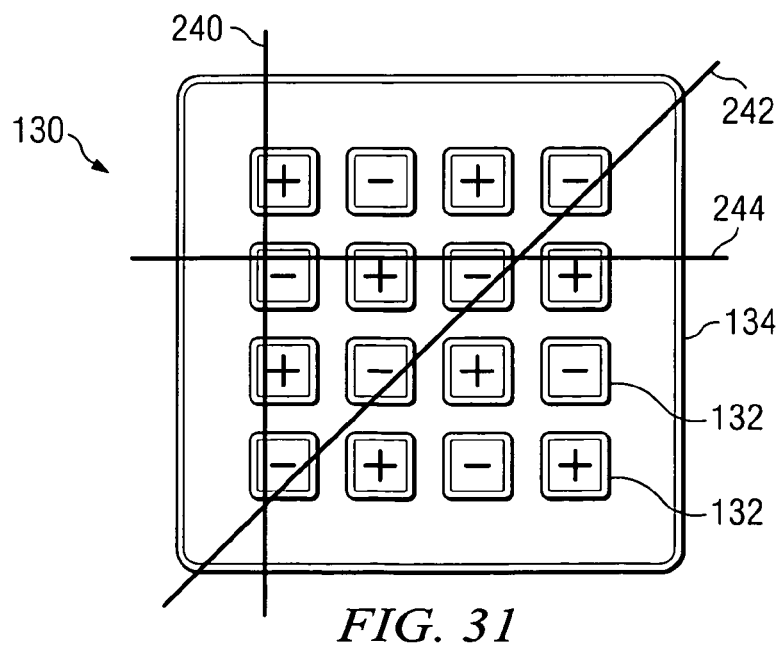
FIG. 31 is an illustration of a possible array of electrode pairs on a probe than can be used with the device.
Figure 42:
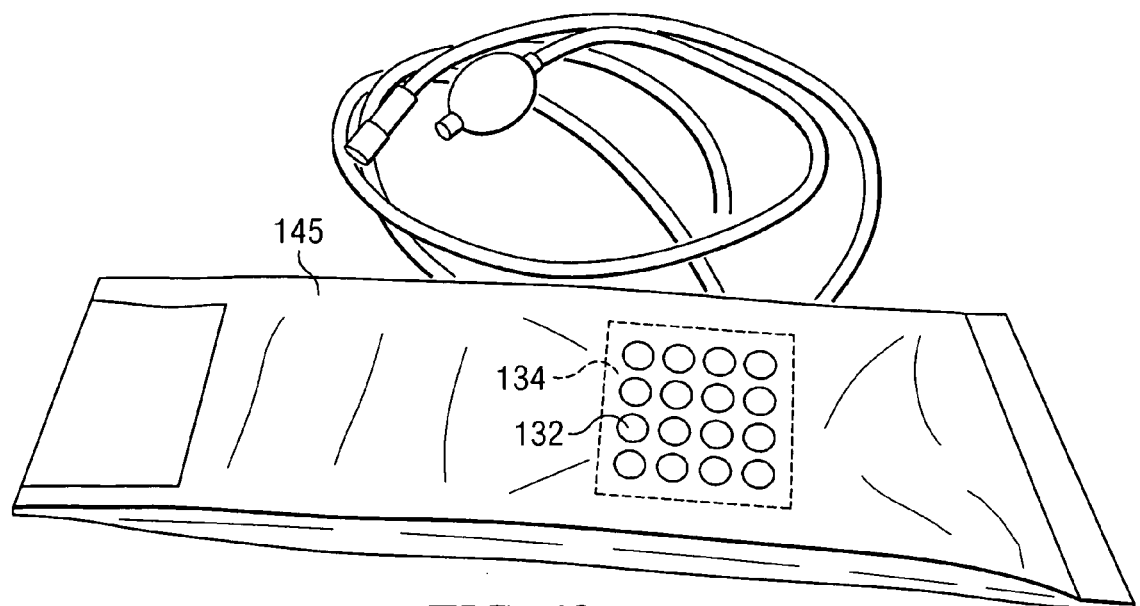
FIG. 42 is a flexible array probe using an inflatable cuff.

FIG. 31 illustrates a probe 130 having a 4 by 4 matrix of electrodes 132. Each electrode 132 has a rounded and contoured shape for effective contact with the skin. The electrodes 132 can be about 1 cm in diameter, for example. The electrodes 132 are mounted on a flexible base 134 which can wrap around a body part, such as an arm or leg. The base 134 can be made of neoprene, for example. The base 134 can be pulled tightly enough around the body member so that at least a majority of the electrodes 132 make contact with the skin. The base 134 can use a mechanism, such as a Velcro closure or belt, to secure the base 134 around the body member. Alternatively, the mechanism can be a bladder 145, such as a blood pressure cuff, that holds the base 134 in place by inflating the bladder 145 as seen in FIG. 42. Increasing the air pressure would increase the pressure exerted by the base 134 on the body member, perhaps increasing the number of electrodes 132 in contact with the skin, and increasing the contact area in contact with the skin. The device can control the air pressure to maintain consistent tissue treatment and maximum patient comfort.

Preferably, adjacent electrodes 132 are of opposite polarity to form electrode pairs. As shown in FIG. 31, the electrodes 132 will alternate +, −, +, − etc. One design provides that all the "+" electrodes 132 are connected together, and all the "−" electrodes are connected together so that the connected electrodes are subjected to the same signal. Thus the area stimulated would be stimulated uniformly (assuming the patient's skin impedance is uniform in that area as well). Another design is to provide individual connections to each of the electrodes 132. This provides the option of a number of enhanced approaches, as discussed hereinafter.

By using individual connections to each electrode 132, it is possible to switch rapidly between pairs of adjacent electrodes or any other pattern selected while using a single pulse generator. It is also possible to switch between adjacent electrode pairs to generate a map of the skin impedance over the entire area contacted by the base 134 prior to actual treatment. This switching can be accomplished either in the device, within the probe or inside a housing that connects to both the probe and the device. This can identify the active areas, allowing the electrodes directly in contact with those active areas to treat the active areas more aggressively. This would eliminate the need to first identify an active area and then place an electrode pair directly on the area. The base 134 would only need to be placed once over the general area of treatment and the multiple electrodes would permit the active areas to be located and treated without further movement of the base 134. The use of multiple electrodes also permits a first area covered by the base 134 to be treated for a predetermined interval, then a second area covered by the base 134 to be treated, and so forth, allowing multiple areas to be treated sequentially without having to reposition the base 134. This would allow an operator to place the base 134 on the patient, initiate the treatment sequence and then attend to other matters as the device cycles through the preset treatment protocol on perhaps several different regions of the patient body sequentially as long as those regions are contacted by electrodes on the base 134.

Figure 19:
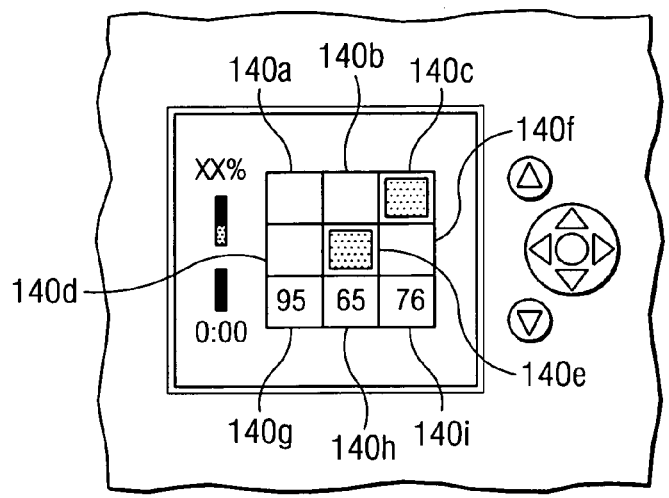
FIG. 19 is a view of the display and selection buttons on a device showing the impedance measured as specific locations on the patient's skin.
Figure 20:
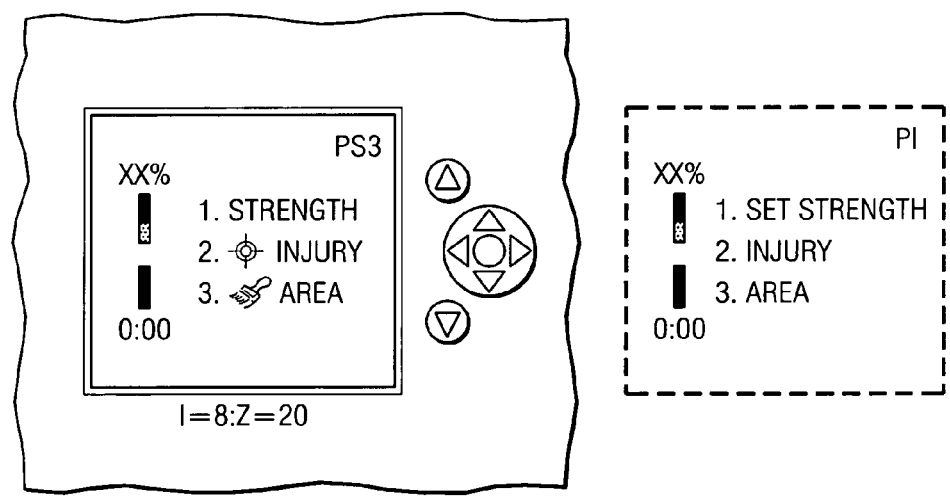
FIG. 20 is a view of the display and selection buttons on a device with a different menu.

The measured skin impedance can be presented to the user in various visual ways. For example, the display 100 could represent the array of electrodes and show different shades in grey scale or different colors to represent the measured impedance. Alternatively, the display 100 can be divided into sectors 140a-i, as seen in FIG. 19 and the actual or relative impedance in each sector (or possibly the averaged impedance in the sector) displayed numerically within the sector.

The distribution and spacing of electrodes can be selected for each application. A circle of electrodes centered about a central electrode can be used, for example. An array of electrodes is believed to deliver more current to a low impedance active site on the skin than would be likely with a single pair of electrodes. Of course, the electrodes must be sufficiently spaced apart from each other to avoid electrode to electrode contact. Preferably, there is at least about a 0.1 inch gap between adjacent edges of any two electrodes and more preferably about a 0.22 inch gap and preferably a gap less than about 0.5 inch and very preferably a gap less than about 1 inch between adjacent edges of any two electrodes. The array of electrodes can also have LEDs spaced in the gaps between the electrodes to allow the user to combine optical treatment with electro-stimulation.

Another advantage of use of multiple electrodes within a base 134 is the possibility of detecting an active area even if the area is not in direct contact with the electrodes. For example, if an array of electrodes is used to generate a map of the impedance of the skin contacted by the electrodes, the impedance values may show a decrease in impedance toward one edge of the base 134, providing an indication that the active area is beyond that edge. The base 134 can simply be repositioned in the direction of the promising indicators, likely over the active area.

Figure 32:
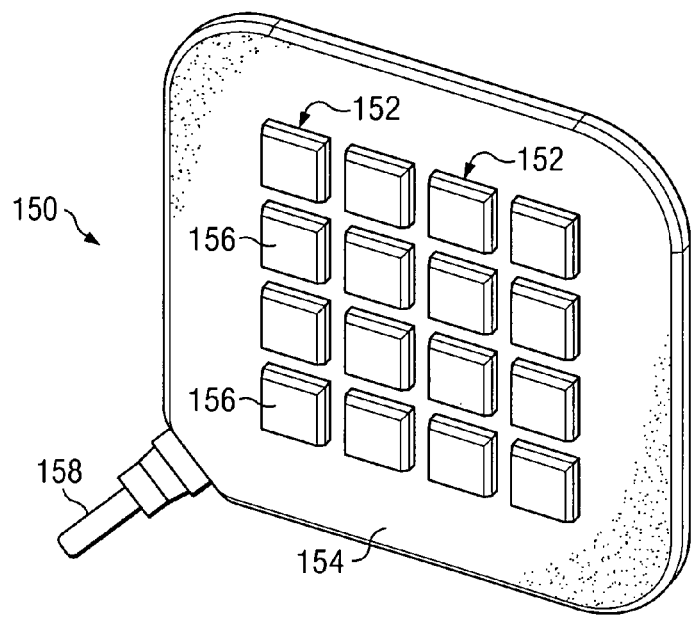
FIG. 32 is a perspective view of a flexible array probe.
Figure 33:
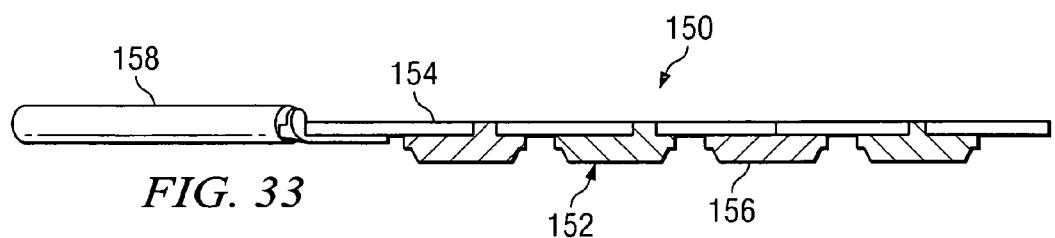
FIG. 33 is a side view of the flexible array probe.
Figure 34:
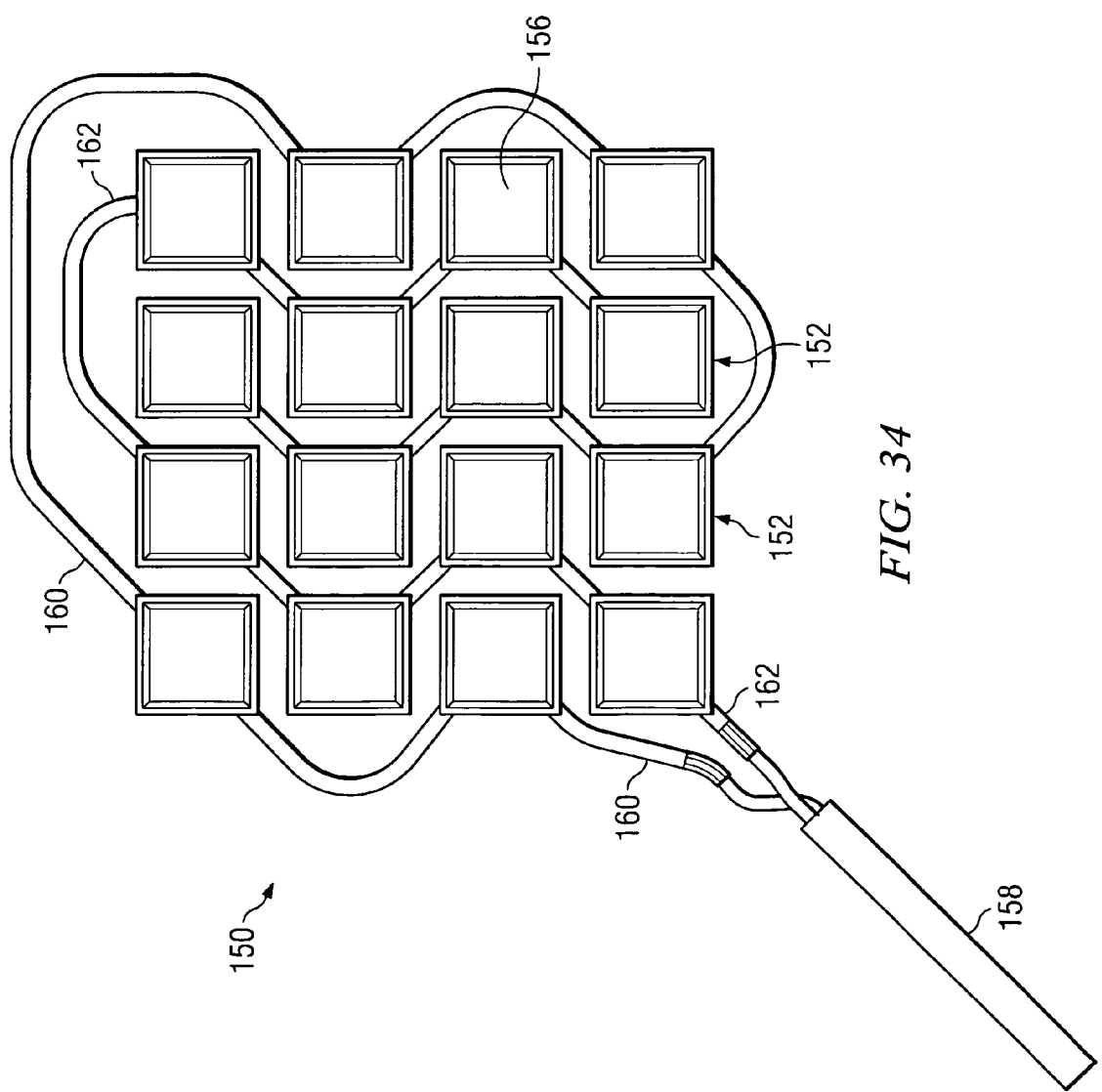
FIG. 34 is an illustration of the circuit of the flexible array probe.

FIGS. 32-34 illustrate a probe 150 having multiple electrodes 152. The individual electrodes 152 have patient contacting surfaces 156 that are formed as squares with sides about 0.6 inches long. Electrodes 152 are separated from adjacent electrodes 152 by about 0.12 inches. Sixteen electrodes 152 are formed in a four by four matrix in the probe 150. The base 154 supporting the electrodes 152 is also a square shape, having sides about 5.0 inches long. Electrodes 152 preferably project out a distance from the inner surface of the base 154, for example ⅛ inch, as shown in FIG. 33, to make better contact with the skin of the patient. The probe 150 is flexible to allow the probe 150 to be wrapped about a portion of the patient. Preferably, both base 154 and electrodes 152 are made of flexible material. For example, base 154 can be formed of non-conductive silicon while the electrodes 152 are formed of conductive silicon. A two conductor cable 158 extends from the probe 150 for attachment to a device, such as devices 10, 50, 70, 80 and 90. One conductor 160 connects to alternate electrodes 152 in the probe 150 while the other conductor 162 connects to the intervening electrodes 152 so that adjacent electrodes 152 are at opposite polarities. Conventional metal wire such as copper can form the portions of conductors 160 and 162 extending to the device, but the portions of conductors 160 and 162 within base 154 are also preferably made of conductive silicon. Two additional conductors can be used that form part of a resistor circuit of predetermined value that is used by the device to which the probe is connected to detect the type of probe.

Figure 48A:
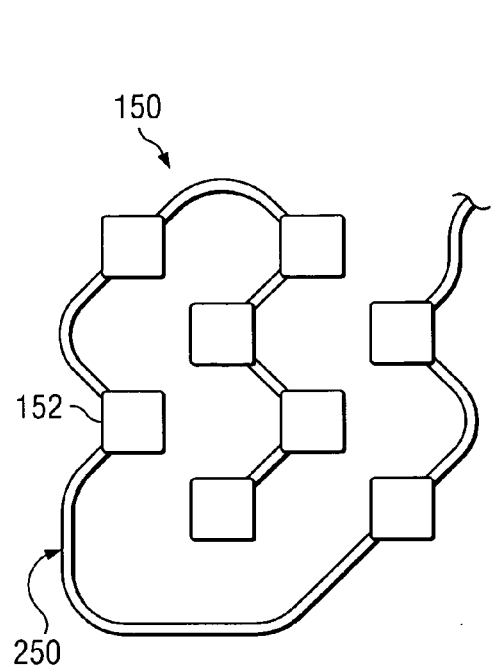
FIGS. 48A-D illustrate the construction of a flexible probe.
Figure 48C:
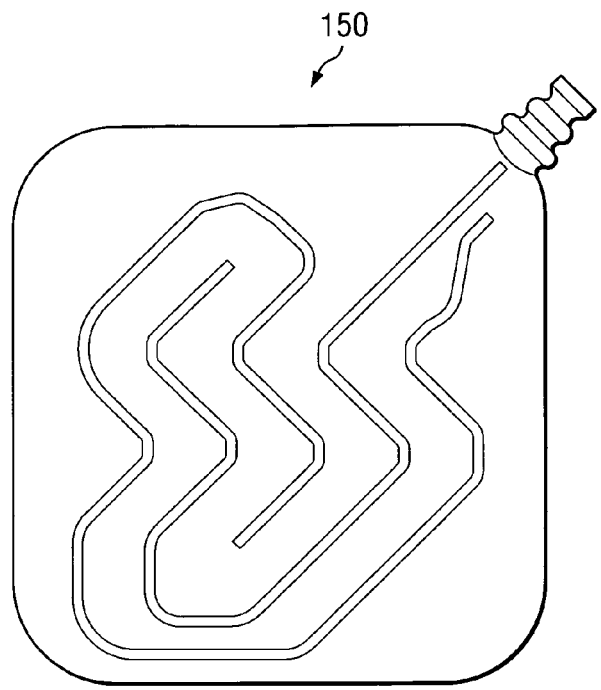
Figure 48B:
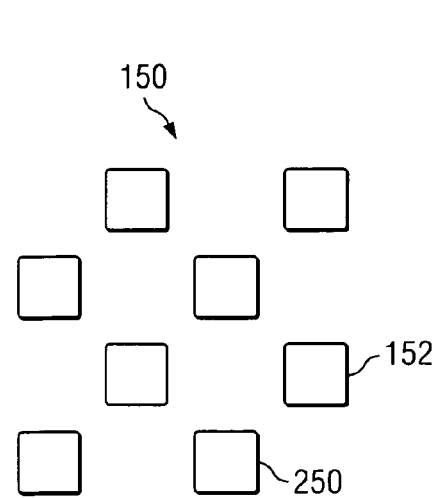
Figure 48D:
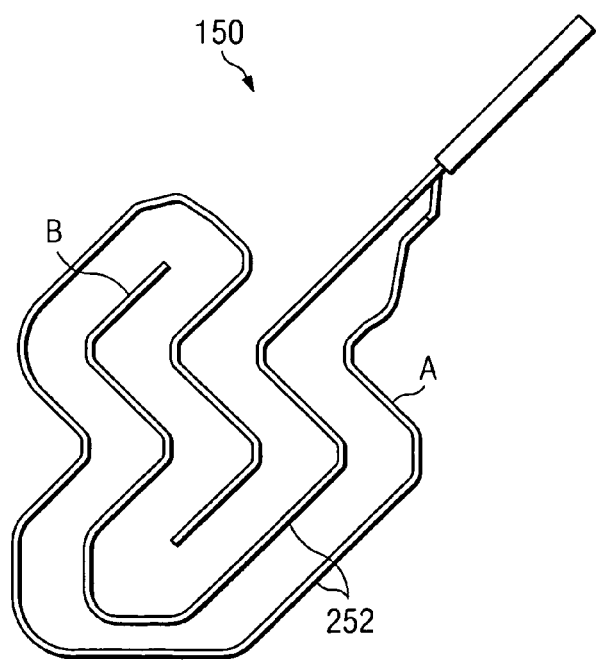

As seen in FIGS. 48A-D, one probe 150 constructed in accordance with the teachings of the present invention utilizes a silver and copper compound doped into the silicon forming electrodes 152 and interconnecting bridges 250 to provide high conductivity to the electrodes 152 and bridges 250. In the probe 150 of FIGS. 48A-D, two separate circuits, circuit A and circuit B, are used to allow for two polarities, with the circuits meshing so that adjacent electrodes are of opposite polarity. A metal conductive wire 252, for example of twisted copper, is routed along each bridge 250 and through each electrode 152 of common polarity to reduce resistance in the circuit. The conductive wire 252 can form part of or be connected to the conductors 160 and 162. In manufacturing the probe 150, a web of the electrodes 152, bridges 250 and conductive wire 252 for each of the circuits A and B are formed first, as seen in FIGS. 48A and 48B. For example, conductive silicon can be molded over a wire 252 bent to the correct shape to form the web. A jig or other alignment mechanism is used to position the webs in the proper orientation to form the probe 150. A non-conductive material, such as un-doped silicone, is then molded around the webs of electrodes 152, bridges 250 and conductive wires 252 to form the final shape of probe 150, as seen in FIG. 48C. The wires 252 not only assist the conductivity of the final probe, but also act as forms to mold the non-conductive material around the webs. The spacing of electrodes in the probe can be critical as the probe is intended to flex to conform to the shape of the body area being treated and if too radical a flexing occurs, electrodes of opposite polarity could actually contact each other and short out the device. Another advantage of use of silver in the electrodes 152 in contact with the skin is its antibacterial characteristics.

Figure 35:
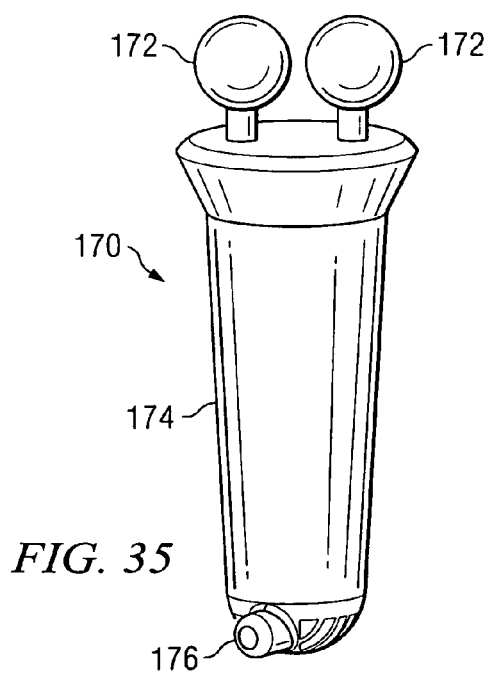
FIG. 35 is a perspective view of a ball probe.

FIG. 35 illustrates a probe 170 having two large ball electrodes 172 extending from a handle 174. A four conductor cable 176 extends from the end of the handle 174 opposite the electrodes 172 for attaching the probe 170 to a device, such as devices 10, 50, 70, 80 and 90. A conductor is connected to each of the electrodes 172 so that the electrodes 172 are at opposite polarities. The remaining two conductors form part of a resistor circuit of predetermined value that is used by the device to which the probe is connected to detect the type of probe. The electrodes 172 are preferably formed of type 316 stainless steel.

Figure 36:
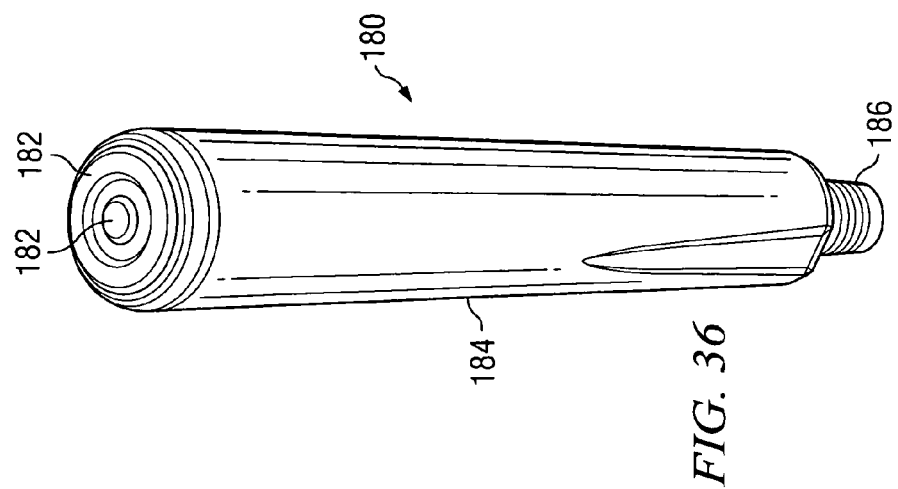
FIG. 36 is a perspective view of a circular electrode probe.

FIG. 36 illustrates a probe 180 having two concentric circular electrodes 182 at one end of a handle 184. A four conductor cable 186 extends from the end of the handle 184 opposite the electrodes 182 for attaching the probe 180 to a device, such as devices 10, 50, 70, 80 and 90. A conductor is connected to each of the electrodes 182 so that the electrodes 182 are at opposite polarities. The remaining two conductors form part of a resistor circuit of predetermined value that is used by the device to which the probe is connected to detect the type of probe. The electrodes 182 are preferably formed of type 316 stainless steel, with the inner electrode about ¼ in diameter and the outer electrode formed of an annulus of inner diameter of about 0.42 inches and an outer diameter of about 0.76 inches.

Figure 37:
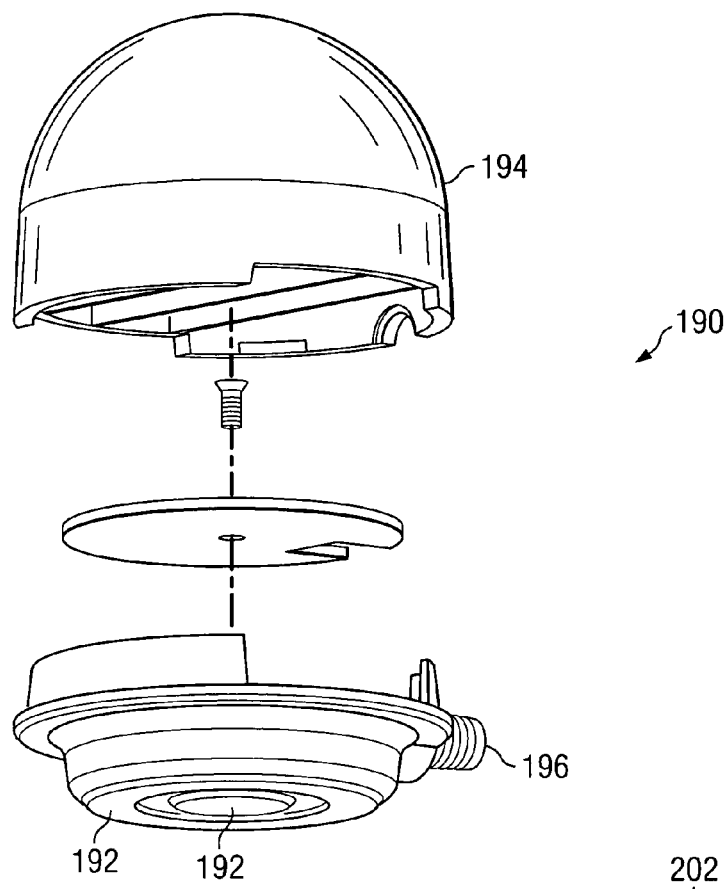
FIG. 37 is an exploded view of a dome probe.

FIG. 37 illustrates a dome shaped probe 190 having two concentric circular electrodes 192 on one side of dome shaped handle 194. It is believed the dome shape of the handle 194 will fit easily into the hand of the probe operator for comfort of use. A four conductor cable 196 extends from the handle 194 for attaching the probe 190 to a device, such as devices 10, 50, 70, 80 and 90. A conductor is connected to each of the electrodes 192 so that the electrodes 192 are at opposite polarities. The remaining two conductors form part of a resistor circuit of predetermined value that is used by the device to which the probe is connected to detect the type of probe. The electrodes 192 are preferably formed of type 316 stainless steel, with the inner electrode about 0.85 inches in diameter and the outer electrode formed of an annulus of inner diameter of about 1.22 inches and an outer diameter of about 2.00 inches.

Figure 38:
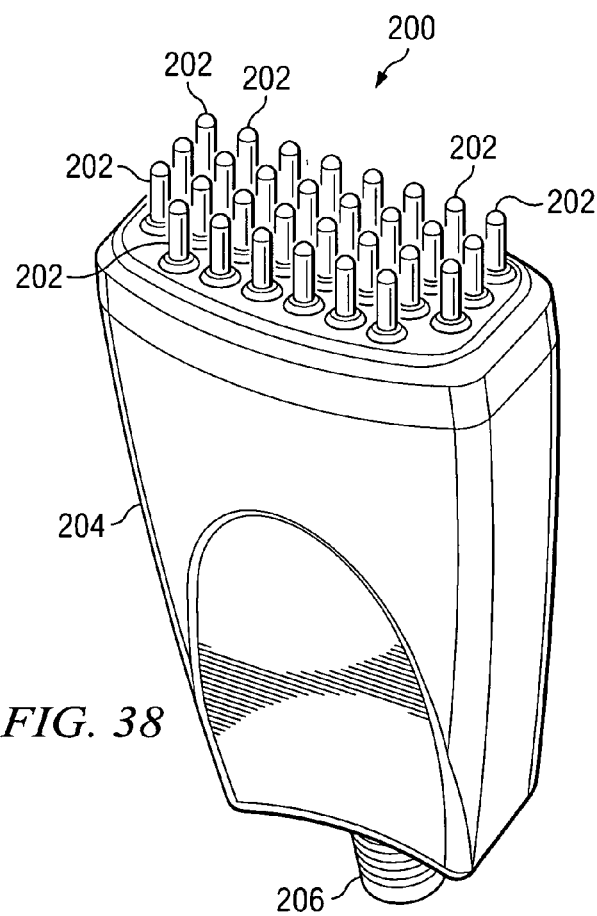
FIG. 38 is a perspective view of a comb probe.
Figure 39:
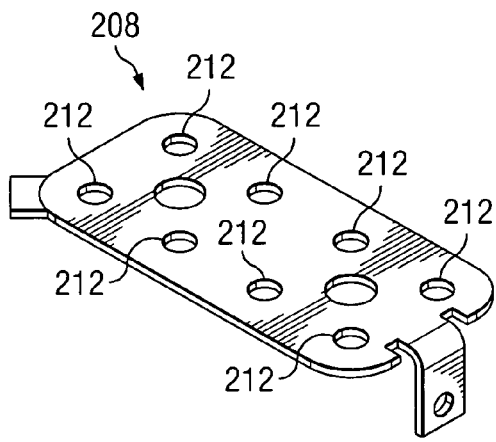
FIG. 39 is a perspective view of the inner electrode plate of the comb probe.
Figure 40:
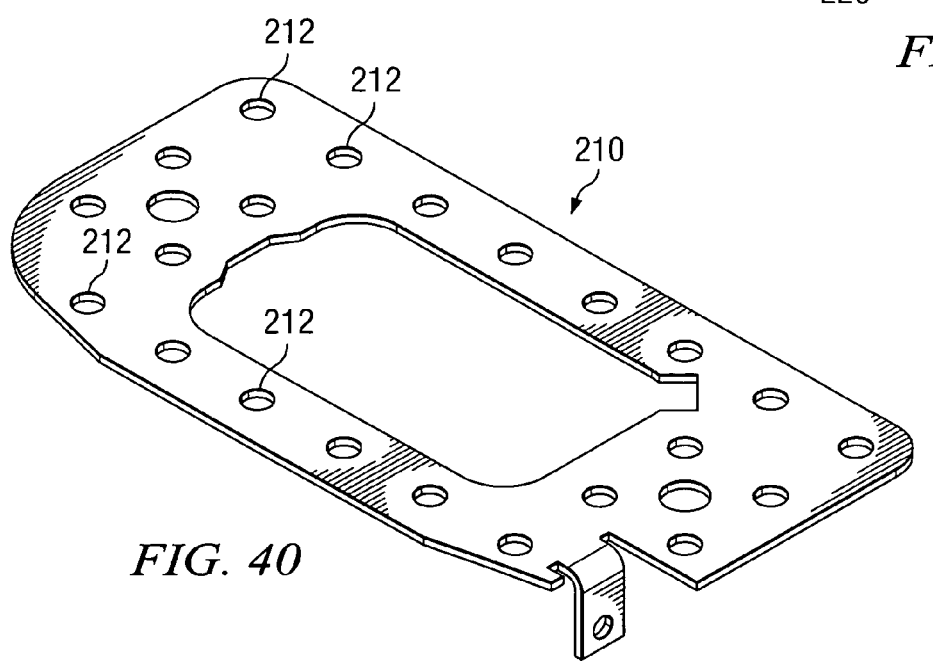
FIG. 40 is a perspective view of the outer electrode plate of the comb probe.

FIGS. 38-40 illustrate a multiple pin comb probe 200 having many pin shaped electrodes 202 forming an electrode array at one end of a handle 204. As seen in FIG. 39, an inner electrode plate 208 mounts eight of the electrodes 202 in apertures 212 in plate 208 near the center of the array. As seen in FIG. 40, an outer electrode plate 210 mounts twenty two of the electrodes 202 in apertures 212 in plate 210 about the outside of the array. A four conductor cable 206 extends from an end of the handle 204 opposite the electrodes 202 for attaching the probe 200 to a device, such as devices 10, 50, 70, 80 and 90. One conductor is connected to inner electrode plate 208 while another conductor is connected to the outer electrode plate 210 so that the pin electrodes connected to inner electrode plate 208 and the pin electrodes connected to outer electrode plate 210 are at opposite polarities. The remaining two conductors form part of a resistor circuit of predetermined value that is used by the device to which the probe is connected to detect the type of probe. The electrodes 202 are preferably formed of type 316 stainless steel, and the inner and outer electrode plates 208 and 210 of copper plated tin. The pin electrodes preferably have a diameter of about 1/16 inch and extend about 0.4 inches above the end of the handle 204, with the array of electrodes 202 being about 1.5 inches wide and 3/7 inches tall. Clearly, any number of pin electrodes 202 can be used, with the shape of the electrode plates 208 and 210 chosen to establish the desired distribution of electrodes in the array.

Figure 41:
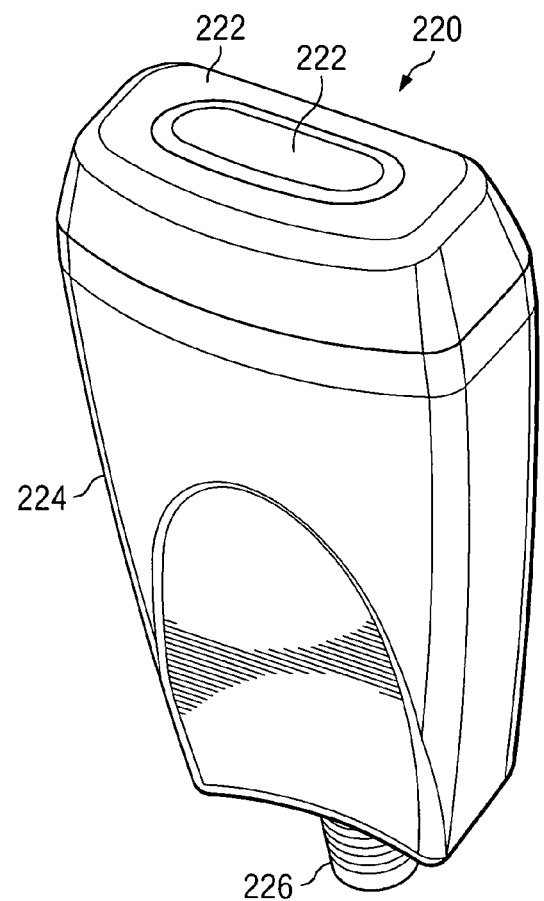
FIG. 41 is a perspective view of a non-circular electrode probe.

FIG. 41 illustrates a probe 220 having two concentric non-circular electrodes 222 at one end of handle 224. A four conductor cable 226 extends from the handle 224 for attaching the probe 220 to a device, such as devices 10, 50, 70, 80 and 90. A conductor is connected to each of the electrodes 222 so that the electrodes 222 are at opposite polarities. The remaining two conductors form part of a resistor circuit of predetermined value that is used by the device to which the probe is connected to detect the type of probe. In probe 220, a 23.2 K Ohm 1/8 watt resistor can be connected between the two conductors in the resistor circuit, for example. The electrodes 222 are preferably formed of type 316 stainless steel, with the inner electrode being roughly a rectangle about 0.91 long and 0.27 inches high and the outer electrode being roughly a rectangle about 1.36 inches long and 0.72 inches high with a roughly rectangular aperture formed in its center larger than the dimensions of the inner electrode.

Figure 44:
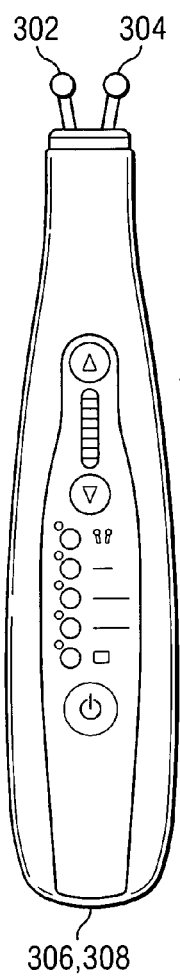
FIG. 44 is a view of a device intended for cosmetic use employing two sets of electrodes.
Figure 45:
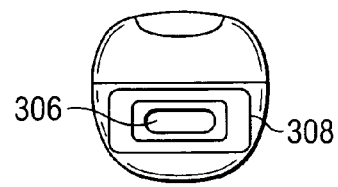
FIG. 45 is an end view of the device of FIG. 44 showing one set of electrodes.

With reference to FIGS. 44 and 45, a modified device 300 is illustrated which is intended for cosmetic use, particularly to treat the face. As can be seen, the device has two different types of electrodes, one at each end. A pulse can be sent to either electrode, depending on the position of a selector switch on the device 300. At one end is an electrode formed by two conductive balls 302 and 304. At the opposite end is an electrode formed by concentric planar electrodes 306 and 308. The operator can use which ever electrode is most effective for the portion of the skin being treated by positioning the selector switch to deliver the pulse to the chosen electrode. For example, the electrode formed by balls 302 and 304 are best suited for treating wrinkle lines in the face, which are formed by the facial muscles. In contrast, the concentric planar electrodes 306 and 308 are best used to treat the planar skin on the face.

As the device 300 is more likely to be used by untrained users, the output of the device 300 may be limited or enhanced to provide parameters that may be specific to the cosmetic treatment. For example, the output of device 300 may be limited to energy levels that are safer for cosmetics than energy levels used to treat injuries. These principles can also be applied to a probe made specifically for use in cosmetics that is used with and attached to one of the devices 10-90 noted above. The device may be designed to recognize the attached probe is a cosmetic probe and automatically lower energy output to a level suitable for cosmetic treatment. If the probe uses ball electrodes, the diameter of the balls may be smaller than in other probes to provide a visual identification that the output energy levels are lower than normal. 15 Hertz is one of the limited outputs when the device is used for cosmetics.

One advantage of devices 10-90 detecting the type of probe attached is that if an unauthorized or improper probe is attached to a device and the device does not recognize the probe as an authorized probe, the device will not operate to send pulses through the probe, providing a safety feature.

Another advantage of devices 10-90 is that they will normally not need to be used with an electro gel, ie a conductive gel of the type used in connecting an EKG device to a patient, that improves the electrical contact between a device and the human skin. However, the skin of some patients may be so dry as to require use of an electro gel with devices 10-90 to provide adequate electrical contact. In essence, the electro gel would be used to return the condition of the skin to a normal, healthy condition for the devices to operate most effectively, much as one would want to wipe off excess moisture before beginning treatment with a device 10-90 from a patient sweating excessively. Clearly, it would not be desirable to use electro gel in a manner to short electrodes of opposite polarity.

Figure 43A:
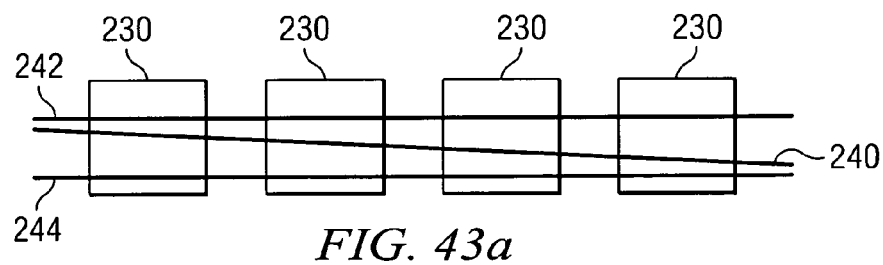
FIGS. 43a and 43b show possible electrode patterns.
Figure 43B:
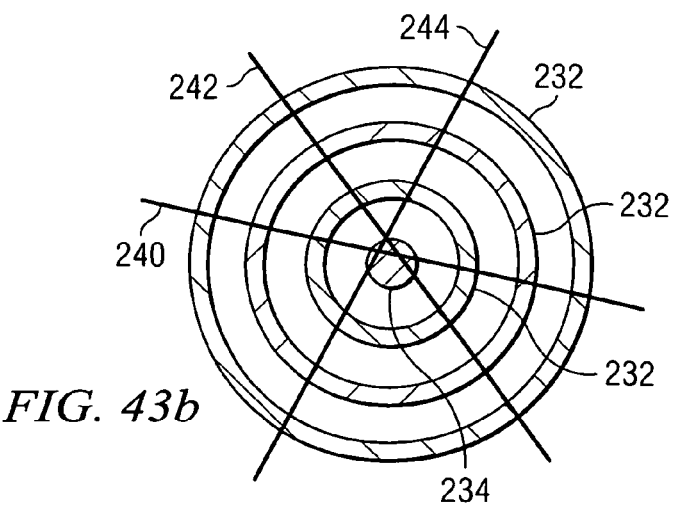

A preferred array of electrodes for use with devices 10-90 will have at least four electrodes, and can be a square array as described above with reference to probes 130 and 150, a line of four or more linear side by side electrodes 230 as seen in FIG. 43a or a series of at least three concentric circular electrodes 232 with a center circular electrode 234, as seen in FIG. 43b, for example. In the preferred array of electrodes, it will be possible to define at least one line in the plane of contact between the electrodes and the skin of the patient which contacts or passes through at least four electrodes. If the electrodes are alternating in polarity, this would correspond to at least three transitions in polarity. For example, if the electrodes are +, −, +, −, transitions occur from + to −, from − to + and from + to − again. Lines 240, 242 and 244 shown in FIGS. 31, 43a and 43b all pass through at least four electrodes, for example.

The devices 10-90 can have indicators, such as displays 100, that tell the user that a probe is connected, the stimulation pattern being applied, the amount of time the device has treated the skin, the strength of the treatment, etc.

Typically, the devices 10-90 will operate in one of three modes, straight, variable, or cycles mode. The straight mode allows stimulation by selecting conditions such as frequency, intensity, number of pulses, modulation, phasing and damping. The variable mode allows variation of certain of the conditions during the course of treatment, such a varying the frequency, damping and modulation. For example, low frequency modulation, low FM, or high frequency modulation, high FM, could be selected. The cycles mode is a sequential series of treatments in the straight, and/or variable mode. For example, a cycles mode could be 5 minutes long and include 2 minutes of a selected straight or variable mode treatment, followed by another 2 minutes of a different selected straight or variable mode treatment followed by a final minute of yet another different selected straight or variable mode treatment or a repeat of the first mode of treatment. A device may allow only certain modes to be used with a given probe. For example, a device may allow only the variable or cycles mode to be used with a particular probe.

Figure 47:
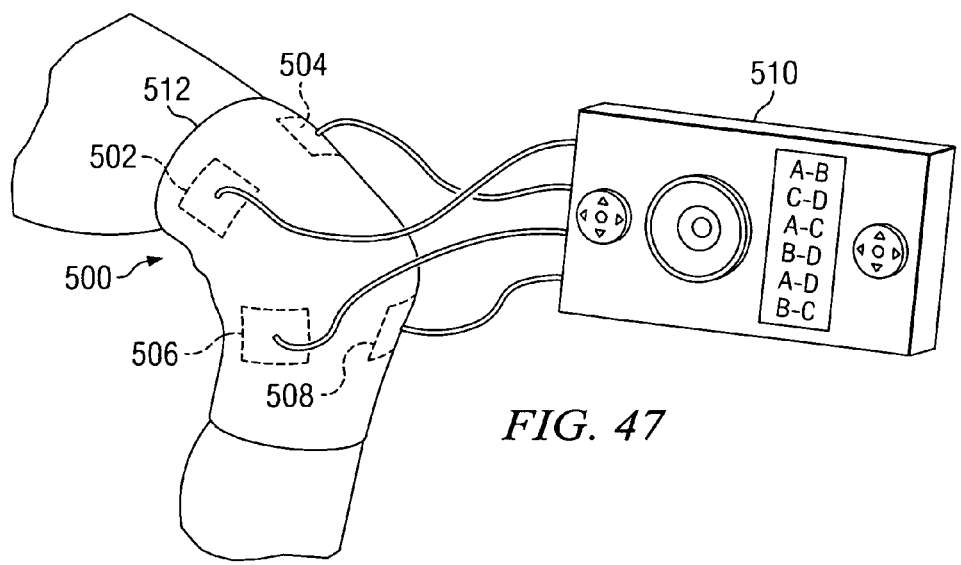
FIG. 47 is an illustrative view of a knee pad probe.

One of the significant advantages of the present invention is that the single pair of electrodes mounted in one of the devices 10-90 can be initially moved over the skin to find an active area and then that area and the surrounding area treated with a multi-pair electrode probe connected to the device and centered on the active area found. While the active area will present the lowest impedance to the probe, the area surrounding the active area covered by the probe will also be treated. That is, the highest current flow into the patient's skin would be expected to occur at the electrodes touching the active area, but smaller currents will also flow into the patient's skin at electrodes touching the skin in the area surrounding the active area. It is believed the simultaneous treatment of the active and surrounding areas is particularly effective. This will clearly reduce the labor required to treat patients. When using only the electrodes mounted in a device (ie, just one pair of electrodes), it would be necessary to treat the active area and then treat or "paint" the surrounding area to attempt to reproduce this treatment. But, of course, it could not be a simultaneous treatment of both the active area and surrounding area, as is possible with a probe. Also, this advantage is realized even when no electrodes are mounted to the device itself, and the electrodes are on probes attached to the device by cables or the like. For example, a single pair electrode probe can be used to locate the active area, and a multiple electrode pair probe can then be used to treat the active and surrounding areas. Such a device is shown in FIG. 47 and described hereinafter. Of course, a multi-pair electrode probe can be used to find an active area and then treat it.

Figure 46:
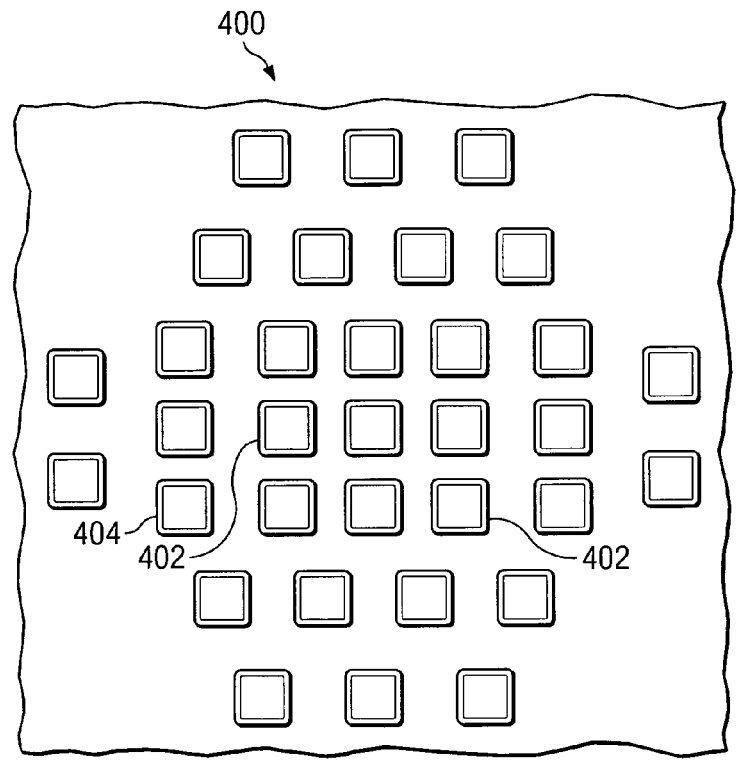
FIG. 46 is an illustrative view of a pad probe with variably spaced electrodes.

A probe 400 is illustrated in FIG. 46 which has variably spaced electrodes. The electrodes 402 near the center of the probe 400 (nine electrodes in a 3×3 array as shown in FIG. 46) are spaced a uniform distance apart. The surrounding electrodes 404 are spaced further apart, as shown. This provides the advantage of concentrating the electrodes over the active area, while decreasing the presence of electrodes over the surrounding, less active areas. As noted, the surrounding areas will be treated to some extent by the surrounding electrodes.

Of course, it is also possible to use the probe itself to find the active area by moving it along the skin and then fixing the probe in the chosen location to perform the treatment. Also, a different probe, for example a smaller locator probe, could be attached to the device and used to locate the active area, with treatment then undertaken with a larger probe to treat both the active and surrounding areas. Also, the electrodes on the device itself may not be suitable for the particular area to be treated and a single electrode pair probe can be used to find the active area, followed by treatment by a multielectrode pair probe.

While the multielectrode pair probe will principally be used in a stationary manner by tightly placing it on the body in a stationary position at the location of the active area, it is also possible to use a multielectrode pair probe in a dynamic manner, that is by moving it across the skin during treatment. In dynamic use, the probe covers a larger area, yet still appears to work well in treating the entire area, and may treat a larger area faster. An advantage of the stationary use is that it can allow unattended treatments. However, it may be preferable to move the multielectrode pair probe dynamically over the body in particular circumstances.

One probe design 500, shown in FIG. 47, is specifically for use on the knee. The probe 500 would have an array of electrodes 502 above the knee and on one side of the knee, with a mirror image array of electrodes 504 on the other side of the knee. An array of electrodes 506 would also be placed below the knee and on one side of the knee, with a mirror image array of electrodes 508 on the other side of the knee as well. Each array can be a 3 by 3 array of electrodes, for example. Each array can be powered by a separate device 10-90 or all the arrays can be powered by a single device 510 as shown. The arrays can be in separate probes and attached separately to the knee, or all the arrays can be mounted in a single probe 512 designed to wrap around the entire knee as seen in FIG. 47.

Figure 49:
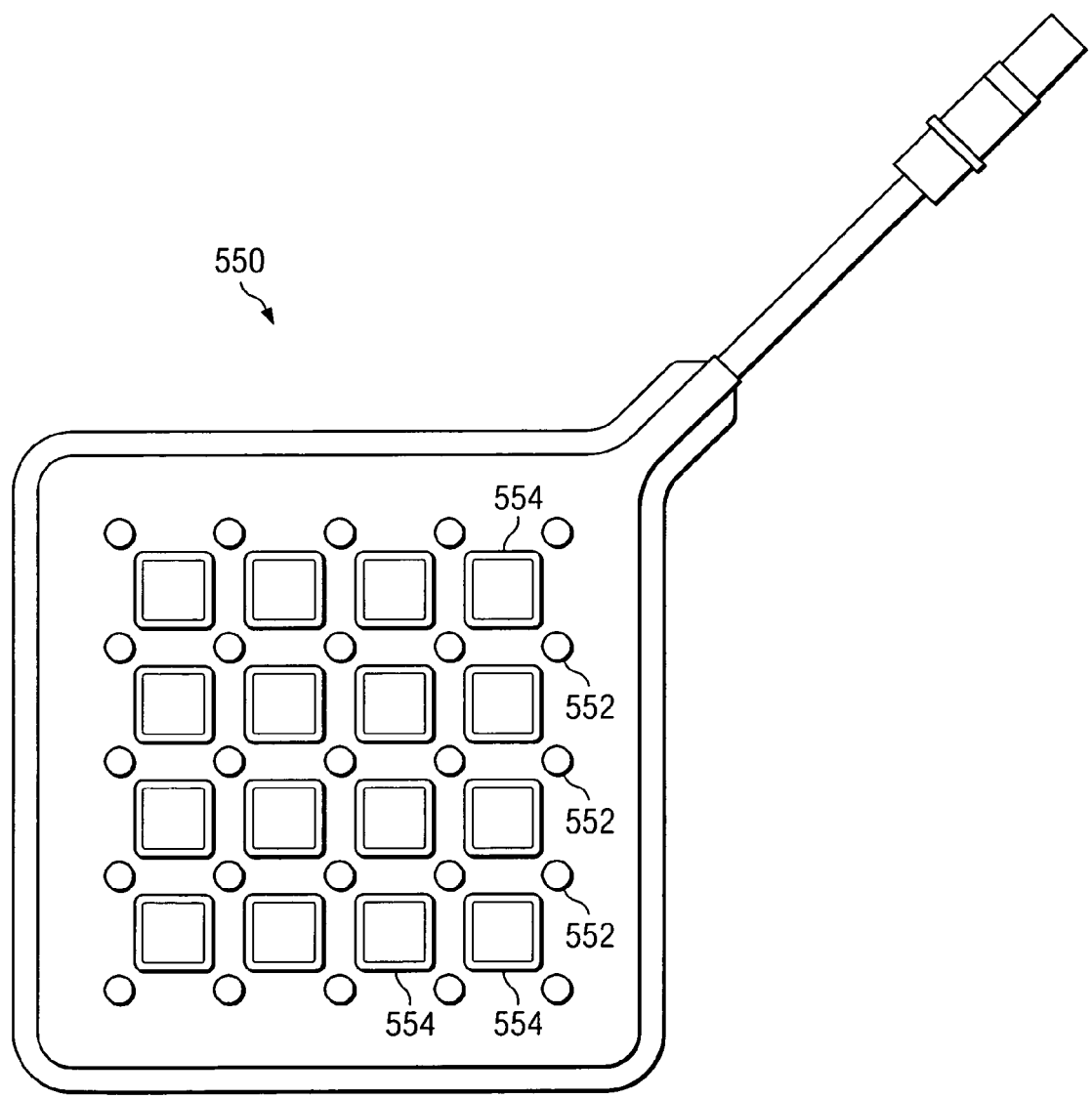
FIG. 49 illustrates a flexible probe using electrodes and light sources.

FIG. 49 illustrates yet another probe design 550 with light sources 552, such as LEDs, positioned between the electrodes 554 to provide the option of treating the patient with both electric pulse and light stimulation.

While several embodiments of the present invention have been illustrated in the accompanying drawings and described in the foregoing Detailed Description, it will be understood that the invention is not limited to the embodiments disclosed, but is capable of numerous rearrangements, modifications and substitutions of parts and elements without departing from the scope and spirit of the invention.

The invention claimed is:

1. An apparatus for treating a patient, comprising:
   a device having a pulse generator for generating a pulse for delivery to the skin of a patient; and
   a control, coupled to the pulse generator, for controlling the pulse generator;
   a plurality of probes adapted to be coupled to the control to deliver the pulse, wherein the plurality of probes comprises a first probe having a first plurality of electrodes in a first electrode configuration and a second probe having a second plurality of electrodes different from the first plurality of electrodes, the second plurality of electrodes being in a second electrode configuration different from the first configuration,
   the control adapted to detect and differentiate between the first and second electrode configurations and provide pulse generator options to a user based on an electrode configuration detected by the control,
   wherein at least one probe is adapted to deliver the pulse to at least a first electrode and a second electrode to determine a relative impedance and determine a treatment area based on the relative impedance, and wherein at least one probe is capable of identifying an active area for treatment and deliver a treatment pulse to the treatment area based at least in part on the relative impedance, and wherein
   at least one probe is adapted to re-direct the treatment pulse based at least in part on a change in the relative impedance.

2. The apparatus of claim 1, the first probe having a first identification element providing a first identification value and the second probe having a second identification element providing a second identification value different from the first identification value, wherein the control recognizes and differentiates between the first and second electrode configurations based on a detected identification value.

3. The apparatus of claim 2 wherein the first identification element is a first resistor and the first identification value is a first resistance value, the control adapted to sense the first resistance value to determine the first electrode configuration.

4. The apparatus of claim 1 wherein at least the first probe is contoured to enable the first plurality of electrodes to evenly contact the skin.

5. The apparatus of claim 1 wherein at least the first plurality of electrodes are formed of conductive silicon, stainless steel or silver.

6. The apparatus of claim 1 wherein at least two adjacent electrodes of the first plurality of electrodes have opposite polarity.

7. The apparatus of claim 1 further comprising at least one LED disposed adjacent an electrode to provide electro stimulation.

8. The apparatus of claim 1 wherein the first probe comprises a pressure cuff to secure the first plurality of electrodes against the skin of the patient, the control adapted to vary a pressure of the pressure cuff to vary contact between the skin and the first plurality of electrodes.

9. The apparatus of claim 1 wherein the first probe is adapted to move over the skin of a patient to determine an active site based at least in part on the relative impedance, and the second probe is adapted to be statically or dynamically placed over or near the active area to treat the active area.

10. The apparatus of claim 1 wherein the first probe is integral with the device.

11. The apparatus of claim 1 wherein the first probe is not integral with the device.

12. The apparatus of claim 1, wherein the pulse generator options comprise a first subset of treatment parameters selected from a predetermined set of treatment parameters and a second subset of treatment parameters selected from the predetermined set of treatment parameters, the first subset of treatment parameters corresponding to the first probe and the second subset of treatment parameters corresponding to the second probe.

13. The apparatus of claim 12 wherein the control is adapted to enable a user to select from a plurality of treatment parameters from among at least the first subset of treatment parameters.

14. An apparatus for treating a patient, comprising:
a device having a pulse generator for generating a pulse for delivery to the skin of a patient;
a control for controlling the pulse generator; and
a patient engaging device having a plurality of electrodes adapted to contact the skin, the control adapted to generate a map of one or more active areas and determine a relative impedance between at least two of the plurality of electrodes to detect an impedance of the skin in contact with the electrodes at specific electrode sites, wherein the patient engaging device is capable of directing stimulation to one or more sites from a selected subset of the plurality of electrodes based at least in part on the determined relative impedance, the patient engaging device further adapted to re-direct stimulation based at least in part on a change in the relative impedance, wherein the control is capable of sequentially directing pulses to treat the one or more active areas at predetermined intervals.

15. The apparatus of claim 14 wherein the device includes a display, wherein treatment areas based on detected skin impedance are represented on the display.

16. The apparatus of claim 14 wherein the control causes the pulse generator to alternate the pulses to selected pairs of the plurality of electrodes.

17. The apparatus of claim 14 wherein the plurality of electrodes comprises at least one first electrode pair mounted in a first probe for movement over the skin of the patient to locate an active area and at least one second electrode pair mounted in a second probe for static or dynamic placement on the skin of the patient at or near the active area to directing a pulse to the active area.

18. The apparatus of claim 17 wherein the first probe is integral with the device.

19. The apparatus of claim 17 wherein the first probe is not integral with the device.

20. The apparatus of claim 19 wherein the first and second probe are the same probe.

21. The apparatus of claim 14, wherein the plurality of electrodes comprises a multi-dimensional array of electrodes, wherein at least one electrode has a polarity opposite of a polarity of a first adjacent electrode adjacent in a first dimension and a polarity opposite of a polarity of a second adjacent electrode adjacent in a second dimension.

22. An apparatus, comprising:
a pulse generator adapted to generate a pulse train to preferentially stimulate nerves rather than muscle;
at least one probe coupled to the pulse generator to transmit the pulse train to the skin of a patient, the at least one probe comprising a plurality of evenly-spaced electrodes arranged in a multi-dimensional array, the array comprising a plurality of electrode pairs, each electrode pair comprising adjacent electrodes having opposite polarities; and
an impedance sensing device adapted to detect an impedance of the skin through the plurality of electrodes and further adapted to determine and map one or more active areas for treatment based on the relative impedance between the plurality of electrode pairs, wherein a configuration of the plurality of electrodes enables the impedance sensing device to identify an optimal treatment area, the configuration further enabling transmission of the pulse train to the optimal treatment area based, at least partially, on the relative impedance between at least two electrode pairs, the configuration further enabling the impedance sensing device to adjust identification of the optimal treatment area, and re-direct transmission of the pulse train, in response to changes in relative impedance between the at least two electrode pairs and the map of the one or more active areas.

23. The apparatus of claim 22 wherein the probe is physically placed onto the skin to provide skin contact with the electrodes.

24. The apparatus of claim 22 wherein the plurality of electrodes comprises a first electrode, a second electrode adjacent the first electrode, and a third electrode adjacent the first electrode and unaligned with the first and second electrodes,
wherein the first electrode has at least first and second edges, each of the first and second edges of the first electrode having a straight portion,
wherein the second electrode has at least one edge having a straight portion,
wherein the third electrode has at least one edge having a straight portion,
the straight portion of the first edge of the first electrode being parallel to the straight portion of the at least one edge of the second electrode, and the straight portion of the second edge of the first electrode being parallel to the straight portion of the at least one edge of the third electrode.

25. The apparatus of claim 24 wherein a distance between the straight portion of the first edge of the first electrode and the straight portion of the at least one edge of the second electrode is substantially equal to a distance between the straight portion of the second edge of the first electrode and the straight portion of the at least one edge of the third electrode.

26. The apparatus of claim 24 further comprising a control adapted to control the pulse generator; and
   a circuit coupled to the control and adapted to deliver the pulse train to the skin, the circuit further adapted to assess the impedance of the skin, and to prevent the pulse train from exceeding a predetermined amount if the assessed impedance drops below a predetermined amount.

27. The apparatus of claim 22 wherein the spacing between electrodes is less than ½ inch.

28. The apparatus of claim 22 wherein the plurality of electrodes remain in a fixed position during treatment.

29. The apparatus of claim 22 wherein the spacing between electrodes is less than 1 inch.

* * * * *